United States Patent [19]

Richards

[11] Patent Number: 4,964,715

[45] Date of Patent: Oct. 23, 1990

[54] COMPARATIVE SURGICAL KERATOMETER

[76] Inventor: William D. Richards, 167 Holliston St., Medway, Mass. 02053

[21] Appl. No.: 310,486

[22] Filed: Feb. 14, 1989

Related U.S. Application Data

[63] Continuation of Ser. No. 15,116, Feb. 17, 1987, abandoned.

[51] Int. Cl.$^5$ .............................................. A61B 3/10
[52] U.S. Cl. .................................... 351/212; 351/211
[58] Field of Search ................ 351/205, 211, 212, 221

[56] References Cited

U.S. PATENT DOCUMENTS 4,046,463  9/1977  LaRussa et al. .................... 351/212
4,660,947  4/1987  Amolis ................................ 351/212

OTHER PUBLICATIONS

Butler, Comparative Surgical Keratometer Report, 10-25-1982.

Primary Examiner—Paul M. Dzierzynski

[57] ABSTRACT

A keratometer designed to be attached to a conventional ophthalimic surgical microscope for use in measuring the power and angle of orientation of an astigmatism of the cornea of an eye. The keratometer comprises an illuminator assembly for reflecting a portion of the coaxial illumination of the microscope so as to generate an annulus of light have radii of curvature identical to the radii of curvature of the cornea. A comparator assembly is also provided for reflecting and modifying a second portion of the coaxial illumination of the microscope so as to generate at least one spherical second annulus of light. The keratometer is arranged to superimpose the second annulus on the first annulus and to cause said superimposed annuli to pass into the objective lenses of the microscope whereby the radius of curvature of the cornea may be determined. Also included is a protractor ring for use in measuring the angle of orientation of the astigmatism. No optical lenses or light sources ae included in the keratometer.

32 Claims, 9 Drawing Sheets

COMPARATIVE SURGICAL KERATOMETER

This is a continuation of Ser. No. 015,116 filed 2-7-87, abandoned.

FIELD OF THE INVENTION

This invention relates generally to devices for measuring the curvature of the cornea of an eye, and more particularly to surgical keratometers of the sort having means for generating an annular reflected corneal image and means for generating and superimposing an annular comparator image over the reflected corneal image whereby the radius of curvature of the cornea may be measured by comparing the corneal image with the comparator image.

BACKGROUND OF THE INVENTION

To perform many ophthalmic surgical procedures, it is essential that the optical properties of the cornea of the eye be known. It is especially important that those optical properties defining the visual defect known as astigmatism (i.e., the power and angle of orientation) be known to properly perform cataract surgery, intraocular lens implantation, radial keratomoty and other ophthalmic surgeries. Accurate information regarding the power and angle of orientation of the astigmatism is essential if the surgeon is to suture the cornea during the surgical procedure in such a manner as to minimize any astigmatism.

Keratometers and ophthalmometers are widely used for measuring the radius of curvature of a cornea. Known keratometers typically reflect a light beam off the convex mirror-like surface of a moist cornea and then process or manipulate the reflected corneal image so as to provide information regarding the astigmatic condition of the eye. Examples of such known keratometers are disclosed in U.S. Pat. Nos. 4046463, 4165744 and 4355871.

Since ophthalmic surgery involves very precise, delicate, and minute incising and manipulation of the corneal tissue, such surgery is generally performed while viewing the cornea through an ophthalmic surgical microscope. In response to this approach to ophthalmic surgery, other keratometers have been developed for use with surgical microscopes. In these keratometers, a reflected corneal image passes through the keratometer before reaching the objective lens of the microscope. See, for instance, U.S. Pat. Nos. 4157859, 4429960 and 4439025.

These and other prior art keratometers typically suffer from at least one of several problems. First, it is frequently difficult (when using the prior art keratometers) to measure the radius of curvature of the cornea with as great a degree of accuracy as may be desired. Second, in the known devices a secondary light source (separate from the light source of the microscope) is generally required to provide the light beam that is reflected off the cornea to generate the reflected corneal image. This secondary light source adds to the cost of the keratometer and often intrudes into the operating work area. Third, the prior art devices are frequently slow or cumbersome to operate and are generally highly complex and, as a result, fairly expensive. Fourth, conventional keratometers frequently provide no means for conveniently determining, in diopters, the degree of astigmatism of the cornea. Finally, known keratometers typically intrude into the surgical operating zone, thereby complicating the surgical procedure.

A prototype comparative surgical keratometer was designed and tested by Herbert F. Butler III as his undergraduate thesis at Massachusetts Institute of Technology ("MIT"). This keratometer is described in the paper "Comparative Surgical Keratometer Report and Zeiss Implementation Proposal" presented at MIT by Mr. Butler on Oct. 25, 1982. The Butler keratometer includes an illuminator assembly for creating an annular light beam to be reflected off the cornea, a comparator assembly for creating a plurality of annular light beam "standards", and means for superimposing a selected annular light beam "standard" on the reflected corneal image. In surgical application, the reflected corneal image and the superimposed "standard" image are transmitted through the microscope for viewing by the surgeon. Using the relative relationship of the superimposed images as a guide, the surgeon sutures the cornea so as to ensure that the reflected corneal image (initially elliptical to the extent that any astigmatism is present) directly overlays and matches the annular "standard" image, thereby eliminating any astigmatism which may have been present.

It was proposed by Butler that the annular light beam transmitted for reflection off the cornea be created by folding a laser beam off an aluminized annulus forming part of the illuminator assembly. The annulus would be formed and positioned to ensure the reflected image intersects the cornea. In implementation, Butler used a circular flourescent light in place of the aluminized annulus.

The Butler keratometer tends to suffer from several problems. First, no means are provided for quantitively measuring the angle of inclination of the astigmatism of the cornea. Second, the illuminator and comparator assemblies are each believed to have separate light sources and to each use a series of optical lenses. By providing separate light sources and lenses for the illuminator and comparator assemblies, the complexity and hence cost of the device is increased. Third, conventional surgical microscopes (with which the Butler keratometer is intended to be used) apparently require substantial modification in order to accept the Butler device.

OBJECTS OF THE INVENTION

One of the objects of the present invention is to overcome the problems and disadvantages associated with prior art keratometers.

Another object of the present invention is to provide a surgical keratometer adapted for use with a conventional surgical microscope and which uses only the illumination source of the microscope and which does not have any illumination source of its own.

Another object of the present invention is to provide a surgical keratometer adapted for use with a conventional surgical microscope and which does not have any lenses of its own.

Another object of the present invention is to provide a surgical keratometer adapted for use with a conventional surgical microscope and which has means for converting a small portion of the coaxial illumination of the microscope into a first annular light beam for reflection off the cornea, means for converting another small portion of the coaxial illumination into a second annular light beam "standard" having one of a plurality of known diameters, and means for superimposing the second annular light beam "standard" onto the reflected corneal image so that the degree of astigmatism in diopters can be calculated.

Another object of the present invention is to provide a surgical keratometer that is relatively simple to make and use and relatively inexpensive to manufacture.

Another object of the present invention is to provide a surgical keratometer which is adapted to be mounted to unmodified conventional surgical operating microscopes, such as those manufactured by Carl Zeiss of West Germany (hereinafter referred to as "Zeiss").

Another object of the present invention is to provide a surgical keratometer which is mountable on a microscope so as to be alternatively slidable into and out of the optical path of the objective lens of the microscope.

Another object of the present invention is to provide a surgical keratometer which includes means for calculating the angle of orientation of the astigmatism.

Another object of the present invention is to provide a surgical keratometer which is of compact size and completely self-contained so as to not undesirably intrude into the operating zone.

Still other objects of the present invention will be described or rendered obvious in the following detailed description of the invention.

SUMMARY OF THE INVENTION

These and other objects of the present invention are achieved by a novel comparative surgical keratometer adapted to (1) divert a first small portion of the coaxial illumination of the microscope to an illuminator assembly wherein the illumination is used to create an annular light beam which is then reflected off the cornea and back into the microscope, and (2) divert a second small portion of the coaxial illumination of the microscope to a comparator assembly wherein one of a plurality of standard light ring images is generated and then superimposed onto the reflected corneal image.

More specifically, the reflected corneal image is generated by folding a small portion of the microscope's coaxial illumination light off a first mirror so as to intersect a second mirror where the light rays are folded again so as to intersect a convex conical third mirror. The light rays are then folded off the conical third mirror so as to intersect an annular fourth mirror formed to project an annular light beam onto the cornea. The light rays reflect off the surface of the cornea generating a reflected corneal image that passes back into the microscope for viewing by a surgeon or technician.

The comparator image is generated by folding a small portion of the coaxial illumination light of the microscope off a fifth mirror so as to pass through a red filter and then through one of a plurality of transparent "standard" images formed on an opaque band. The band is indexable so as to permit selective alignment of one of the "standard" images with the red filter. The light passing through an aligned one of the "standard" images intersects a sixth mirror where it is folded so as to intersect a pair of seventh mirrors where it is folded again so as to pass back into the microscope where it appears superimposed onto the reflected corneal image for viewing by the surgeon or technician.

The present keratometer has a mounting bracket adapted for engagement with the dovetail mounting fixture of the Zeiss ophthalmic surgical microscope. Included on the mounting bracket is a slidable carriage assembly for allowing the keratometer to be alternatively moved into and out of axial alignment with the objective lens of the microscope.

DESCRIPTION OF THE DRAWINGS

Still other objects and features of the present invention will be more fully disclosed or rendered obvious in the following detailed description of the preferred embodiment, which is to be considered together with the accompanying drawings wherein like numbers refer to like parts and further wherein.

DETAILED DESCRIPTION OF THE INVENTION

Figure 1:
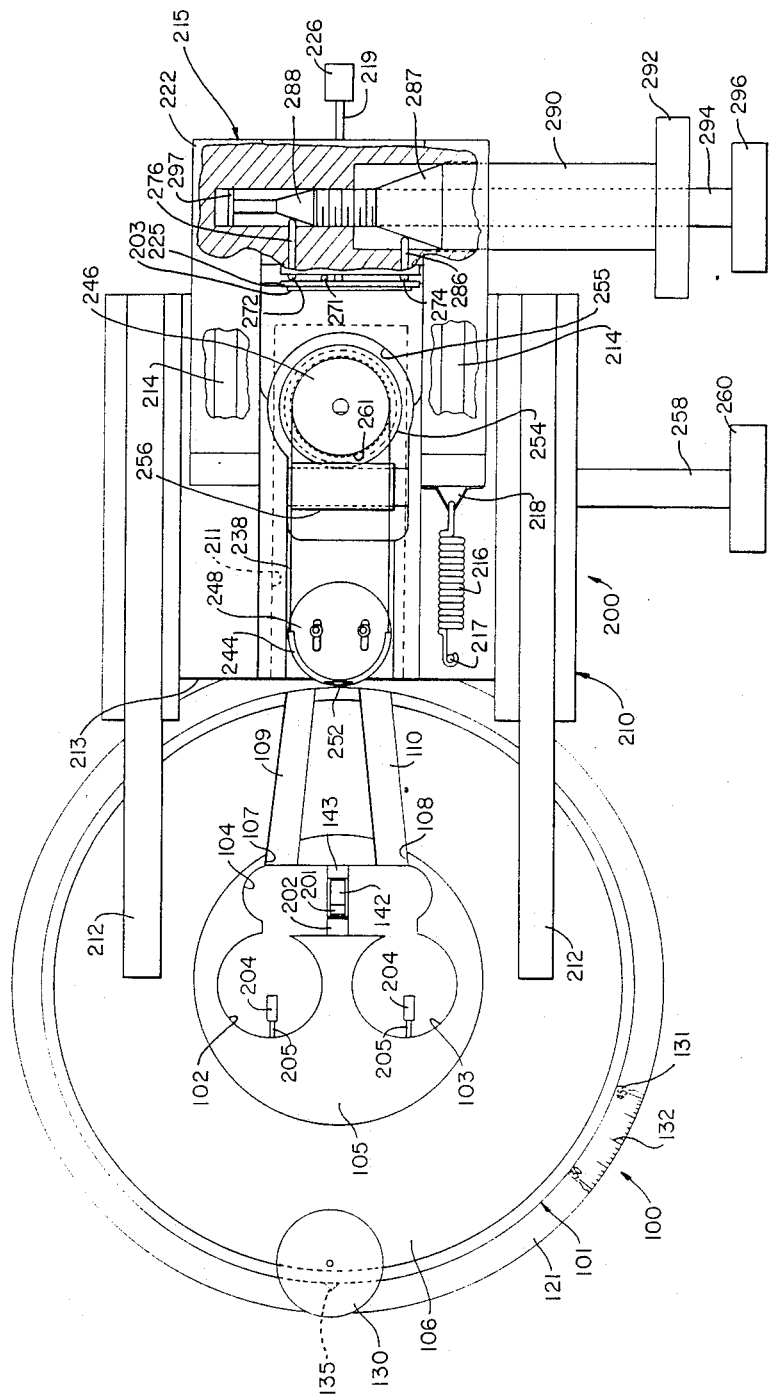
FIG. 1 is a plan view of the top side of the keratometer of the present invention, with the slidable mounting bracket removed to facilitate description of the device.
Figure 2:
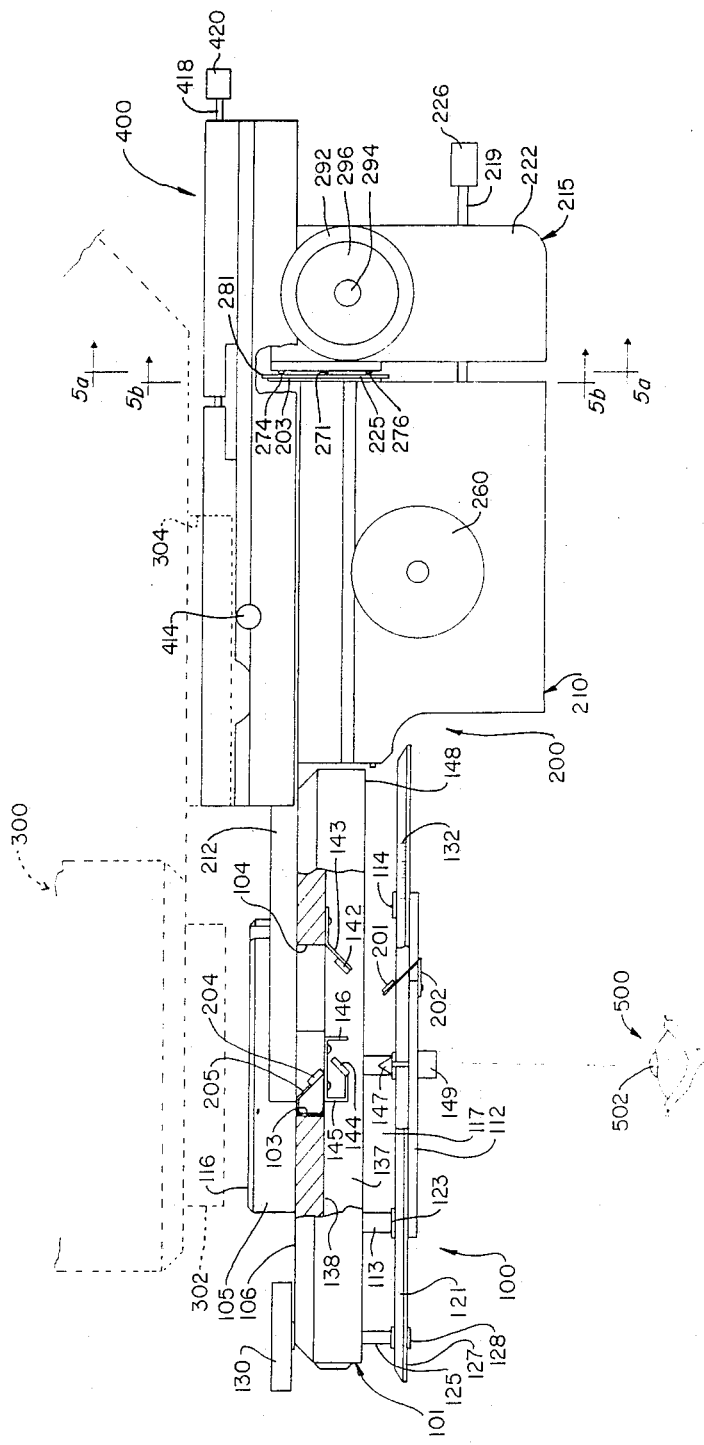
FIG. 2 is a side elevation view of the keratometer.

Looking first at FIGS. 1 and 2, the present invention generally comprises an illuminator assembly 100 and a comparator assembly 200. While separately identified, these assemblies 100 and 200 function in tandem and together provide a comparator image superimposed on a reflected corneal image, as described hereinafter. The illuminator assembly 100 and comparator assembly 200 are secured beneath the objective lens of a microscope 300 (FIG. 2) by slidable carriage assembly 400. The superimposed comparator and reflected corneal images may be passed into the microscope 300 so as to permit viewing thereof during microscopic examination of an eye 500. A variety of materials may be advantageously employed in the manufacture of the keratometer of the present invention, the only requirements being that the materials be manufacturable so as to achieve a relatively rigid structure and that the materials be suitable for withstanding autoclaving or chemical sterilization.

Figure 3:
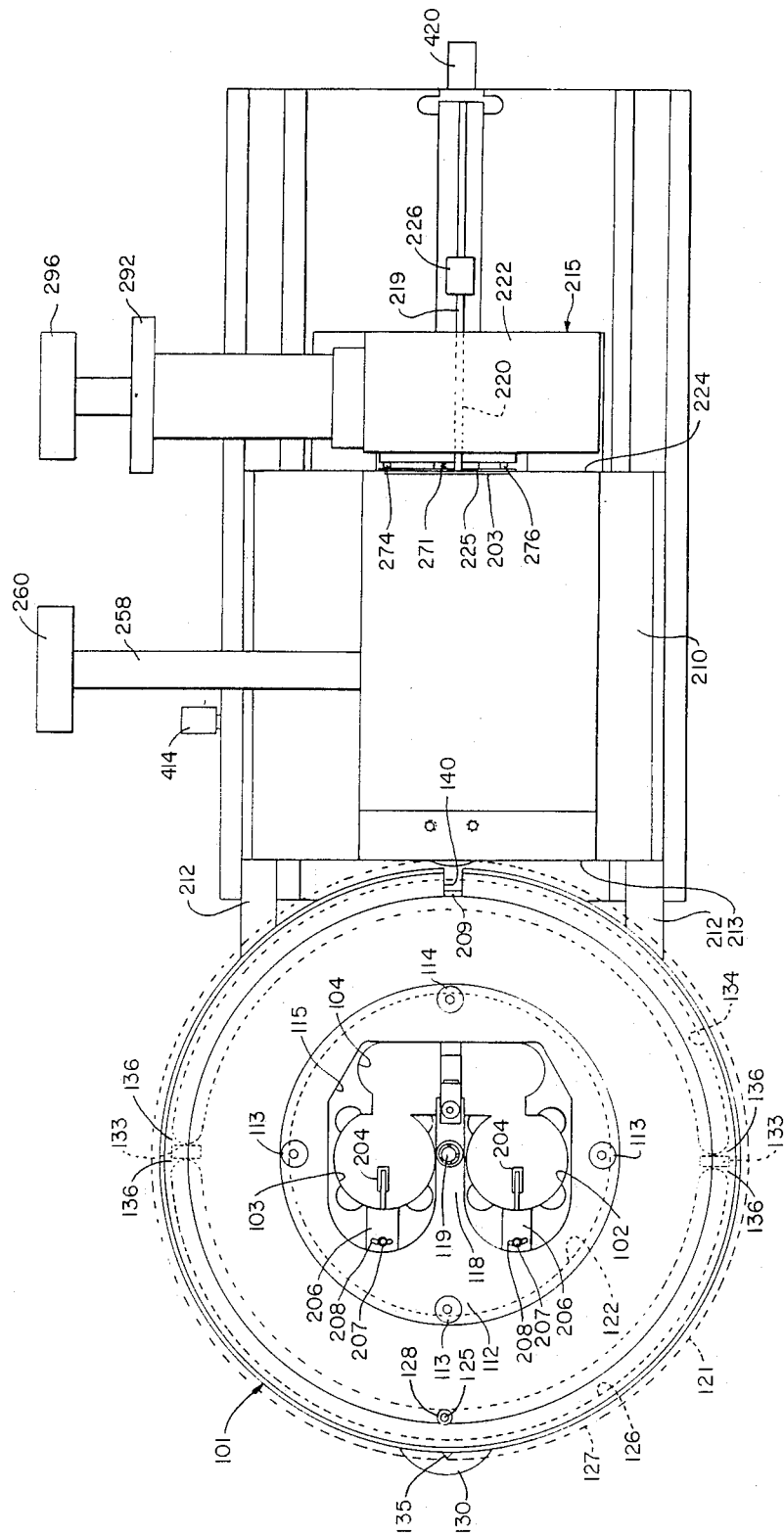
FIG. 3 is a plan view of the bottom side of the keratometer.

Looking next at FIGS. 1-3, illuminator assembly 100 comprises a circular housing 101 having circular apertures 102 and 103 formed therein. Apertures 102 and 103 extend entirely through housing 101 and are disposed on opposite sides of the center of housing 101 so as to lie along a diameter of the housing. Apertures 102 and 103 are sized and spaced relative to one another so as to be coaxially aligned with the microscope's binocular objective lenses 302 (only one of which is shown in FIG. 2) when the keratometer is affixed to the microscope as described hereinafter. An oblong aperture 104 is also formed in (and extends entirely through) housing 101. The long dimension of oblong aperture 104 extends in parallel with that diameter of housing 101 along which apertures 102 and 103 are disposed. Oblong aperture 104 is spaced radially from the aforementioned diameter so as to intersect the peripheral edges of apertures 102 and 103 whereby oblong aperture 104 and apertures 102 and 103 are connected to one another so as to form one large aperture. Apertures 102, 103 and 104 are provided to permit passage of direct and reflected light through circular housing 101, as described hereinafter.

Circular housing 101 includes a raised portion 105 (FIGS. 1 and 2) which extends above top surface 106 of the housing. Raised portion 105 is preferrably formed integrally with housing 101 and circular apertures 102 and 103 and oblong aperture 104 extend entirely through raised portion 105. Openings 107 and 108 (FIG. 1) are formed to extend entirely through the wall of raised portion 105 so that the portion of oblong aperture 104 (FIG. 1) disposed in raised portion 105 opens outwardly to top surface 106. Grooves 109 and 110 are formed in the housing's top surface 106 so as to intersect and extend entirely through openings 107 and 108, respectively. Openings 107 and 108 and respective grooves 109 and 110 are provided to allow reflected light to communicate with apertures 102, 103 and 104, as described hereinafter.

A circular plate 112 (FIGS. 2 and 3) is secured to the bottom of circular housing 101 by three posts 113. Posts 113 are disposed adjacent the peripheral edge of circular plate 112 and are sequentially spaced at 90 degree increments so as to be disposed at the 90 degree, 180 degree and 270 degree positions, as seen in FIG. 3. A fourth post 114, which is attached to circular plate 112 but which does not extend so as to be connected with circular housing 101, is disposed at the 0 degree position, as seen in FIG. 3.

An aperture 115 (FIG. 3) is formed in plate 112 so as to lie directly below circular apertures 102 and 103 and oblong aperture 104. By this placement of plate aperture 115, an opening is created that extends from the top surface 116 (FIG. 2) of raised portion 105, through apertures 102, 103 and 104, through space the 117 (FIG. 2) located between circular housing 101 and circular plate 112, and through aperture 115. A finger 118 (FIG. 3) of plate 112 extends into aperture 115 slightly past the midpoint 119 thereof so as to bisect a portion of aperture 115. Aperture 115 is disposed so that midpoint 119 is coincident with the center of circular housing 101.

An annular protractor ring 121 (FIGS. 1-3) is rotatably secured to plate 112 so as to be coaxial with circular housing 101 and rotatable about midpoint 119. Circular inner edge 122 (FIG. 3) of ring 121 slidingly engages posts 113 and 114. Referring particularly to FIG. 2, protractor ring 121 is sandwiched between plate 112 and radially extending sleeves 123 which are fastened to posts 113, whereby ring 121 is prevented from moving axially as it is rotated. Sleeves 123 extend radially from posts 113 approximately one eighth inch (⅛").

A shaft 125 (FIGS. 2 and 3) is rotatably disposed in circular housing 101 and extends downwardly from housing 101 into a curved slot 126 (FIG. 3) formed in protractor ring 121. Curved slot 126 extends in parallel with and is positioned radially inwardly from the peripheral edge 127 (FIGS. 2 and 3) of protractor ring 121. A friction sleeve 128 is secured to the lower end of shaft 125 and disposed in slot 126 so as to frictionally engage the inner edge of the slot. A knurled adjustment knob 130 is secured to the opposite end of shaft 128. Rotation of knob 130 causes friction sleeve 128 to rotate, and sleeve 128 in turn causes protractor ring 121 to rotate by virtue of its frictional engagement with the inner edge of curved slot 126.

Angular degree numerals 131 and gradation marks 132 are affixed to the peripheral edge 127 of protractor ring 121 adjacent curved slot 126, as shown in FIGS. 1 and 2 (for convenience of illustration, angular degree numerals 131 and gradation marks 132 are shown to extend over only a portion of the entire circumference of ring 121). Preferably, the numerals 131 run in fifteen degree increments from 0 to 180 degrees, whereupon they start over and again run from 0 to 180 degrees (the 0 and 180 degree positions being coincident and identified as 180 degrees). The location of each angular degree is identified by an angular gradation mark 132. A pair of radially extending slots 133 (FIG. 3) are formed in protractor ring 121 between the ends of curved slot 126 and another like curved slot 134. Solid sections 136 of annular protractor ring 121 are formed between curved slots 126 and 134 and the radially extending slots 133. Radially extending slots 134 are formed in protractor ring 121 adjacent peripheral edge 127 so as to be radially aligned with the two 90 degree numerals 131.

An alignment mark 135 (FIGS. 1 and 3) is formed on the outer surface of circular housing 101 beneath knob 130 and in radial alignment with post 114, one of the posts 113 and shaft 125, as seen in FIG. 3.

Looking now at FIGS. 2 and 4, the bottom portion of circular housing 101 includes a cylindrical cavity 137 defined in part by an upper surface 138 and an annular mirror 139 which will hereinafter be described in further detail. A slot 140 (FIG. 3) is formed in annular mirror 139 and extends completely through circular housing 101.

Turning now to FIGS. 1-4, illuminator assembly 100 also comprises a plurality of mirrors.

A first mirror 142 is secured by a bracket 143 to the upper surface 138 of the cylindrical cavity 137. First mirror 142 is disposed in cavity 137 beneath the midpoint of the long dimension of oblong aperture 104, whereby first mirror 142 is in axial alignment with the coaxial illumination light source of the microscope when the apertures 102 and 103 are aligned with the focal axis of objective lenses 302, as will be hereinafter described. First mirror 142 is disposed in cavity 137 so that its reflective surface extends at an approximately 45 degree angle to the plane of upper surface 138.

A second mirror 144 is secured by a bracket 145 (FIG. 2) to upper surface 138 of cylindrical cavity 137. Second mirror 144 is positioned above midpoint 119 of circular housing 101 (FIG. 3) so as to lie on the longitudinal axis of circular housing 101. Second mirror 144 is disposed in cavity 137 so that its reflective surface extends at an approximately 45 degree angle to the plane of upper surface 138. Bracket 145 includes a tab 146 (FIG. 2) formed so as to extend between first mirror 142 and second mirror 144. An aperture (not shown) is formed in tab 146 to permit a portion of the light that is reflected off first mirror 142 to intersect second mirror 144, as described hereinafter.

A convex conical third mirror 147 is disposed in space 117 (FIG. 2) so as to be aligned with midpoint 119 and so as to be on the longitudinal axis of circular housing 101. The apex of conical mirror 147 is positioned closer to the bottom surface 148 (FIG. 2) of circular housing 101 than is the base of mirror 147. The entire conical outer surface of mirror 147 is reflective, and the outer surface forms an acute angle of approximately 45 degrees with the vertical axis of the conical mirror 147. Conical mirror 147 is secured to a mounting sleeve 149 (FIG. 2) that is affixed to finger 118 (FIG. 3) of circular plate 112. Preferrably, conical mirror 147 is secured to sleeve 149 by means of threads, whereby conical mirror 147 may be moved toward or away from bottom surface 148 so as to permit proper generation of the reflected conical image, as described below. It is to be appreciated that such positional adjustment of conical mirror 147 is typically made only at the time of manufacture of the keratometer and not by end users of the device.

Annular mirror 139 constitutes a fourth mirror in the illuminator assembly. As noted previously, annular mirror 139 helps define cylindrical cavity 137. Mirror 139 extends entirely around the peripheral edge of cavity 137, except where it is penetrated by slot 140. Slot 140 is positioned so as to be diametrically opposed to alignment mark 135. Annular mirror 139 is disposed so that its reflective surface forms an acute angle of approximately 45 degrees with bottom surface 148 of housing 101.

Looking next at FIGS. 1-4, comparator assembly 200 comprises a fifth mirror 201 (FIG. 2) which is disposed in space 117 so as to lie beneath the midpoint of the long dimension of oblong aperture 104. Fifth mirror 201 is secured by a bracket 202 to finger 118 so that its reflective surfaces form an acute angle of approximately 45 degrees with surface 138. As with first mirror 142, fifth mirror 201 is positioned so as to be in axial alignment with the coaxial illumination of microscope 300 when apertures 102 and 103 are positioned beneath objective lenses 302 as described hereinafter.

First mirror 142 and fifth mirror 201 are disposed along the radius of circular housing 101 that intersects slot 140. A red transluent filter 209 (FIG. 3) is secured in slot 140 to filter out all but the red rays of any light passing through the slot.

A sixth mirror 203 is disposed astern of circular housing 101 and will hereinafter be described in detail.

A pair of seventh mirrors 204 (FIG. 2) are disposed within circular apertures 102 and 103 so as to be in axial alignment with the centers of the apertures. Seventh mirrors 204 are secured to triangular brackets 205 (FIGS. 2 and 3) that are secured inside of apertures 102 and 103 opposite the openings that connect the apertures with oblong aperture 104. On account of this positioning, the reflective surfaces of seventh mirrors 204 form acute angles of approximately 45 degrees with top surface 116 (FIG. 2) of raised portion 105. Preferably, triangular brackets 205 are secured to adjustment plates 206 (FIG. 3) that are secured to surface 138 of housing 101 by set screws 207 that extend through curved slots 208 formed in plates 206. Adjustment plates 206 are secured via screws 207 and curved slots 208 to permit radial adjustment of seventh mirrors 204 within apertures 102 and 103, whereby the mirrors are alignable with the long dimension of grooves 109 and 110 (FIG. 1) to reflect light as described hereinafter.

Brackets 202 and 205 (as well as the aforementioned brackets 143 and 145) are preferably made from corrosion resistant sheet metal or other relatively rigid malleable material. By selectively bending brackets 202 and 205 (as well as the aforementioned brackets 143 and 145), the corresponding respective mirrors 201 and 204 (as well as the aforementioned mirrors 142 and 144) secured thereto may be aligned to reflect light as described below. It is to be appreciated that such alignment is intended to be done at the time of manufacture of the present device, and not by the end users of the device.

While a mirror 204 has been described as being disposed in each of the apertures 102 and 103, it is to be appreciated that only one mirror 204 need be provided in only one of the apertures 102 and 103. When only one mirror 204 is provided, the one of the grooves 109 and 110 extending toward the one of circular apertures 102 and 103 in which the mirror is not disposed is blocked.

Comparator assembly 200 also comprises a comparator housing 210 (FIGS. 1-3) having a cavity 211 (FIG. 1) formed therein. Comparator housing 210 is secured to a pair of long rails 212 that are in turn secured to top surface 106 of circular housing 101, whereby the comparator housing 210 is disposed in spaced fixed relation to the circular housing 101. Long rails 214 are secured to comparator housing 210 and circular housing 101 so that the front edge 213 (FIGS. 1 and 3) of housing 210 is disposed parallel to and spaced from the diameter of housing 101 along which circular apertures 102 and 103 lie.

A pair of short rails 214 (shown in the breakaway views of FIG. 1) are secured to comparator housing 210 so as to extend between and parallel to long rails 212. A mirror carriage 215 (FIGS. 1-3) slidably engages short rails 214 so as to be slidable therealong. Mirror carriage 215 is biased toward front edge 213 of comparator housing 210 by a coil spring 216 (FIG. 1). A first end of spring 216 is secured to comparator housing 210 by a stud 217 (FIG. 1) and the second end of the spring is secured to a bracket 218 (FIG. 1) that is secured to mirror carriage 215.

A threaded shaft 219 (FIGS. 1-3) is disposed in a threaded bore 220 (FIG. 3) formed in the rear portion 222 (FIGS. 1-3) of mirror carriage 215 so as to extend in parallel with short rails 214. Shaft 219 extends entirely through rear portion 222 and one end of the shaft contacts the rear surface 224 (FIG. 3) of comparator housing 210. Manipulation of a knob 226 secured to the opposite end of shaft 219 causes mirror carriage 215 to move, under the bias of spring 216, toward or away from circular housing 101 depending upon the direction in which knob 226 is rotated.

Figure 4:
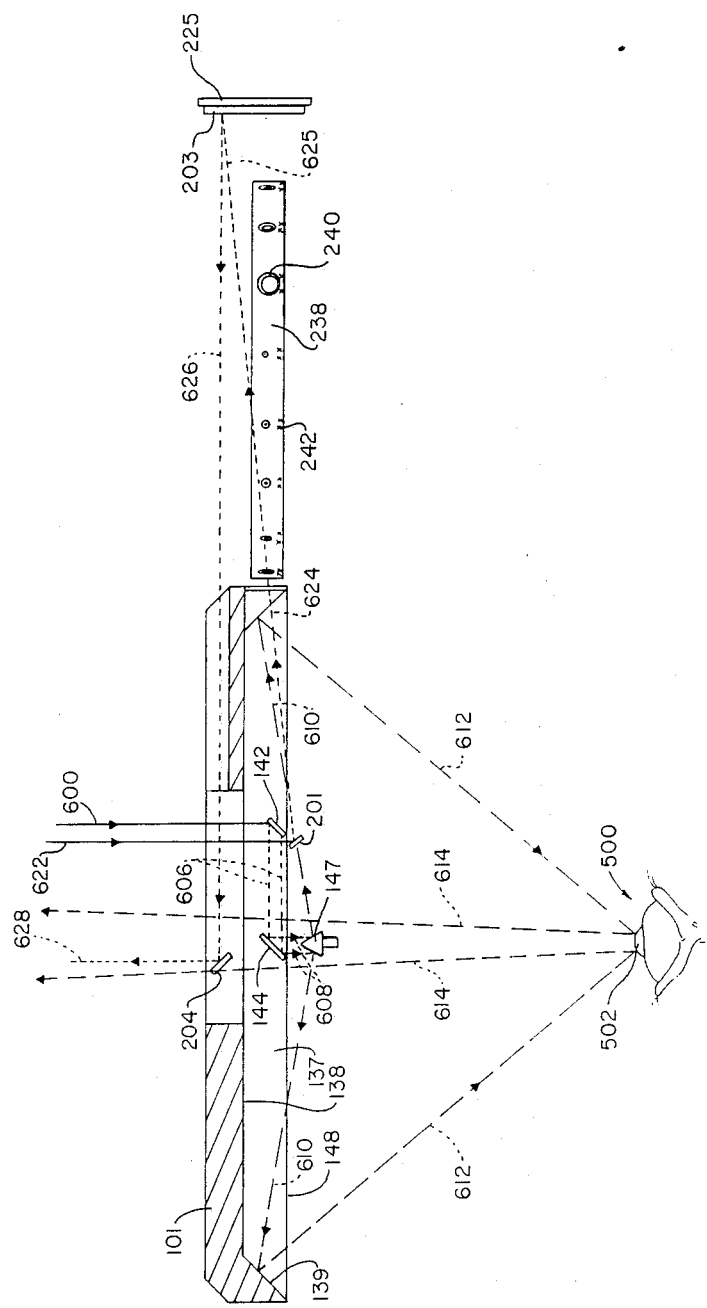
FIG. 4 is a schematic representation showing how the light rays are folded to produce the reflected corneal image and the comparator image.

Referring now to FIGS. 1, 3 and 4, comparator assembly 200 also comprises a continuous opaque comparator band 238 (FIGS. 1 and 4) on which a plurality (e.g. thirty-two) of transparent rings 240 (FIG. 4) of successively increasing size are formed. A transparent numerical optical power equivalent 242 (FIG. 4) representing the optical power in diopters of an annular comparator image created via rings 240 (as described below) is formed on band 238 adjacent each ring 240 (it is to be appreciated that the relative diameters of adjacent rings 240 have been exaggerated in FIG. 4 to illustrate that the size of rings 240 increases successively from smallest to biggest). Band 238 is preferably made of photographic film having rings 240 and numbers 242 formed thereon by conventional photographic processes. Alternatively, band 238 may be made of a thin stainless steel strip with rings 240 and numbers 242 formed thereon by chemical etching. The diameter of rings 240 is selected so as to permit the creation of an annular comparator image of selected size, as described hereinafter.

Continuous comparator band 238 is supported for indexable movement on a curved fixed guide 244 (FIG. 1) and on a rotatable hub 246 (FIG. 1). Fixed guide 244 extends vertically upward from a base plate 248 (FIG. 1) to which it is secured, and base plate 248 is in turn secured to the floor of the cavity 211 formed in comparator housing 210. A slot 252 (FIG. 1) is formed in the curved fixed guide member 244 so as to intersect an extension of the aforementioned radius along which first mirror 142 and fifth mirror 201 lie.

Rotatable hub 246 is secured to rotate with a circular gear 254 (FIG. 1) that is rotatably mounted beneath hub 246 to the floor of a second cavity 255 (FIG. 1) formed in the floor of cavity 211. A cylindrical drive gear 256 (FIG. 1) is disposed in second cavity 255 so as to drivingly engage circular gear 254. A shaft 258 (FIGS. 1 and 3) is rotatably disposed in comparator housing 210 so that one end thereof extends into cavity 211 and is connected to cylindrical drive gear 256. A knurled knob 260 is secured to the opposite (i.e., outboard) end of shaft 258. Rotation of knob 260 rotates shaft 258 which in turn rotatably drives the cylindrical drive gear 256 that drives circular gear 254 that rotates rotatable hub 246. Rotation of rotatable hub 246 in turn causes continuous comparator band 238 to move about an oval path whereby successive ones of rings 240 and diopter numbers 242 are aligned with the slot 252 formed in fixed guide 244.

Preferably a plurality of radially extending teeth 261 (FIG. 1) are formed on a peripheral edge of rotatable hub 246, and a plurality of slots (not shown) are formed adjacent an edge of comparator band 238. Band 238 is mounted on rotatable hub 246 so that teeth 261 on the hub engage the corresponding slots on the band so as to facilitate the transmission of movement from hub 246 to band 238.

Figure 5A:
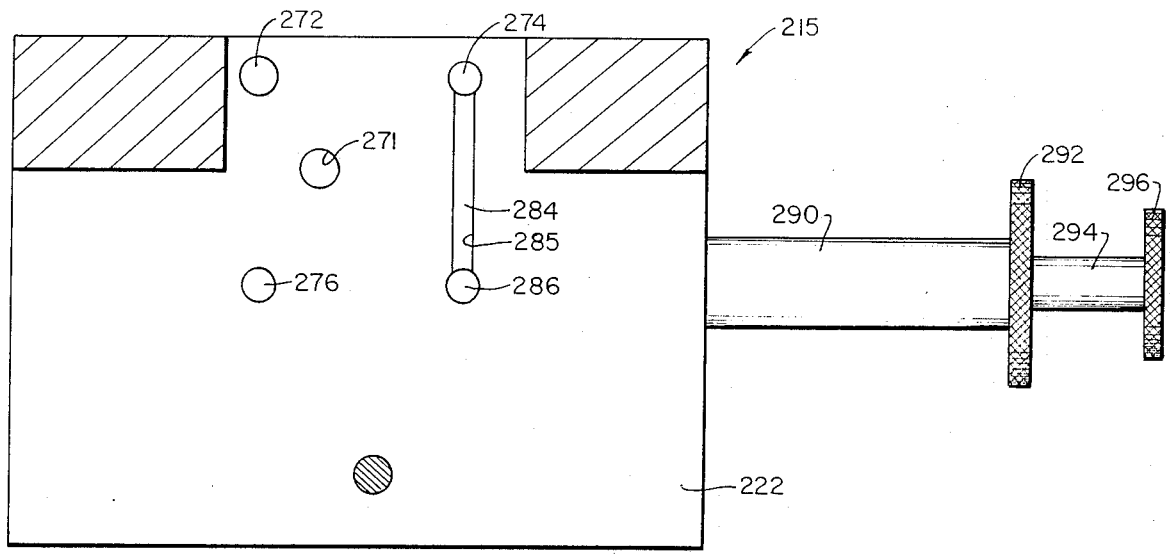
FIG. 5a is a cross-sectional view taken along line 5a—5a in FIG. 2.

Referring now to FIGS. 1-4, 5a and 5b, sixth mirror 203 (see particulary FIGS. 1 and 4) is secured to a mounting plate 225 that is in turn adjustably secured to the rear portion 222 of mirror carriage 215 so as to be adjustable through three planes. A coil spring 271 (FIGS. 1, 5a and 5b) is secured to both the rear portion 222 of mirror carriage 215 and mounting plate 225 so as to urge the mirror 203 toward rear portion 222 and against a ball 272 (FIGS. 1 and 5a), an elongated upper finger 274 (FIGS. 1 and 5a) and an elongated lower finger 276 (FIG. 5a). Preferably, one end of coil spring 271 extends into an aperture 277 (FIG. 5b) formed mounting plate 225 and is secured thereto by a pin 278 (FIG. 5b) that extends across aperture 277 and is held against the mounting plate 225 by the bias of coil spring 271.

Ball 272 is disposed between mounting plate 225 and the rear portion 222 of mirror carriage 215 in an aperture 279 (FIG. 5b) formed in a first corner of the mounting plate. The diameter of aperture 279 is slightly less than the diameter of ball 272 so as to ensure that ball 272 remains disposed behind the first corner of mounting plate 225. Preferably, ball 272 is also seated in a detent (not shown) formed in the rear portion 222 of mirror carriage 215 in direct alignment with aperture 279.

Figure 5B:
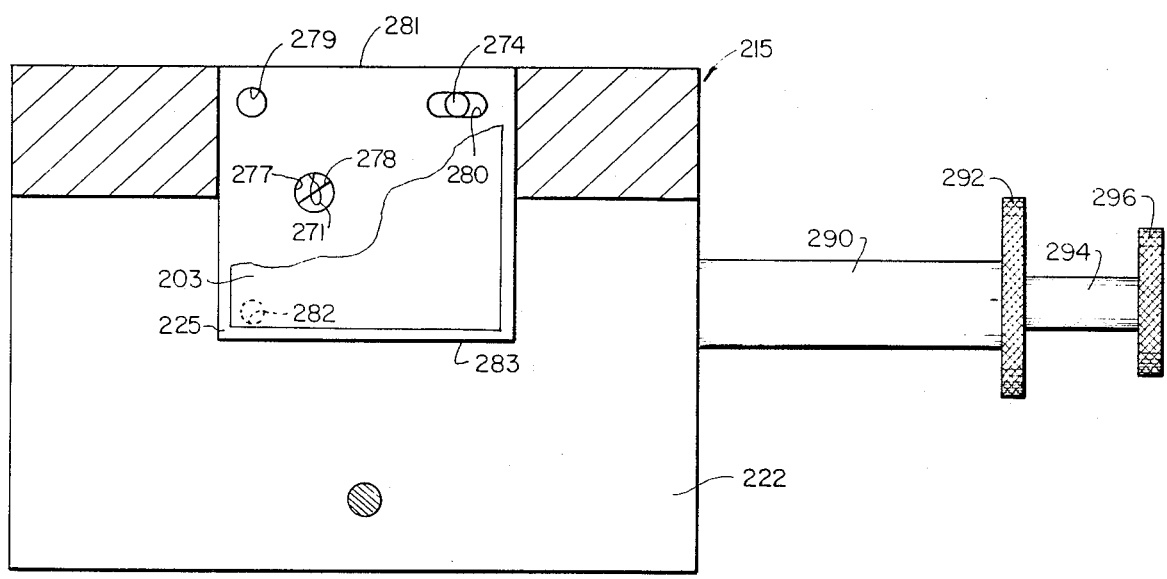
FIG. 5b is a cross-sectional view taken along line 5b—5b in FIG. 2.

Upper finger 274 extends axially outwardly from rear portion 222 so as to engage a slot 280 (FIG. 5b formed in a second corner of mounting plate 225. The width of slot 280 is slightly less than the cross-sectional thickness of finger 274, whereby the finger remains disposed in, but does not extend through, slot 280. Ball 272 and upper finger 274 engage mounting plate 225 along a first axis that extends parallel to and adjacent to a top edge 281 (FIGS. 2 and 5b) of mounting plate 225.

Elongate lower finger 276 (FIGS. 2 and 3) extends axially outwardly from rear portion 222 so as to engage a detent 282 (FIG. 5b) formed in a third corner of mounting plate 225. Finger 276 is positioned directly beneath ball 272 and lies along a second axis that extends parallel to and adjacent to a bottom edge 283 (FIG. 5b) mounting plate 225.

Fingers 274 and 276 are mounted in rear portion 222 of mirror carriage 215 so as to be reciprocally movable along their axes (by means described hereinafter) toward and away from sixth mirror 203. Axial movement of upper finger 274 causes the second corner of mirror 203 to move toward and away from rear portion 222; axial movement of lower finger 276 causes the third corner of mirror 203 to move toward and away from rear portion 222. It is to be appreciated that inasmuch as coil spring 271 holds the first corner of mounting plate 225 in constant engagement with ball 272 and holds ball 272 in constant engagement with rear portion 222, adjustment of upper finger 274 and lower finger 276 permits adjustment of mirror 203 through two planes. It is to be appreciated that the slidable engagement of the tapered nose (not shown) of upper finger 274 in oval slot 280 (FIG. 5) prevents mirror 203 from rotating when adjusted by the axial reciprocation of upper finger 274 and lower finger 276.

A linkage 284 (FIG. 5a) is disposed in a slot 285 (FIG. 5a) which is formed in mirror carriage portion 222 so as to extend perpendicular to mirror top edge 281. An auxiliary finger 286 (FIGS. 1 and 5a) is mounted in rear portion 222 of mirror carriage 215 so as to be reciprocatable along its axis toward and away from mirror 203. Elongate upper finger 274 is secured to one end of linkage 284, and auxilary finger 286 is secured to the other end of the linkage so that upper finger 274 and auxiliary finger 286 extend perpendicular to, but in opposite directions away from, linkage 284. Auxiliary finger 286 does not engage mounting plate 225. Instead, axial movement of auxiliary finger 286 toward mirror 203 is transmitted to linkage 284 so as to cause the latter to move toward the mirror. This movement of linkage 284 is transmitted to upper finger 274 so as to cause the latter to move axially toward sixth mirror 203 and thereby urge the second corner of the mirror away from the rear portion 222 of the mirror carriage 215. Axial movement of auxiliary finger 286 away from mirror 203 likewise causes the second corner of the mirror to move toward rear portion 222. Lower finger 276 and auxiliary finger 286 lie along the aforementioned second axis that extends parallel to and adjacent to bottom edge 283.

Referring now to FIG. 1, various sections of the rear portion 222 of mirror carriage 215 have been removed to reveal the mechanism for causing lower finger 276 and auxiliary finger 286 to reciprocate axially. The principal operative elements of the mechanism comprise a large cone 287 and a small cone 288. Large cone 287 is attached to one end of a hollow large shaft 290 and a knob 292 is secured to the other end of shaft 290. Shaft 290 is threadedly received in rear portion 222 of mirror carriage 215 so that the longitudinal axis of shaft 290 extends perpendicular to the longitudinal axis of auxiliary finger 286 and so that large cone 287 engages auxiliary finger 286. A small shaft 294 is slidably coaxially received in the hollow large shaft 290 so as to extend through the apex of large cone 287. A knob 296 is secured to one end of small shaft 294 and small cone 288 is secured to the other end of small shaft 294. Small shaft 294 is also threadedly received in rear portion 222 of mirror carriage 215 and small cone 288 engages lower finger 276. A disk 297 is secured to the apex of small cone 288 and is rotatably disposed in a cylindrical cavity (not shown) formed in rear portion 222 having a diameter slightly greater than the diameter of disk 297 whereby radial movement or runout of small shaft 294 is prevented.

Regarding the adjustment of sixth mirror 203, rotation of knob 292 in a clockwise direction causes large shaft 290 and large cone 287 secured thereto to move axially toward auxiliary finger 286. By this axial movement, auxiliary finger 286 slides along the outer surface of large cone 287 toward the base of the cone whereby the finger is moved toward mirror 203. Rotation of knob 292 in a counterclockwise direction causes large cone 287 to move axially away from auxiliary finger 286 thereby permitting the finger to slide along the surface of large cone 287 toward the apex whereby finger 286 moves away from mirror 203. Auxiliary finger 286 is moved away from mirror 203 under the bias of coil spring 271 transmitted from the spring to mounting plate 225, then to upper finger 274, then to linkage 284 and finally to finger 286. Thus, clockwise rotation of knob 292 causes the second corner of mirror 203 to move away from rear portion 222 and counterclockwise rotation of knob 292 causes the second corner of the mirror to move toward rear portion 222.

In a like manner, clockwise rotation of knob 296 causes small cone 288 to move axially towards lower finger 276. This axial movement causes finger 276 to slide along the outer surface of cone 288 toward the base thereof whereby the finger is urged toward mirror 203. By this movement of lower finger 276, the third corner of mirror 203 is urged away from rear portion 222 of mirror carriage 215. Rotation of knob 296 in a counterclockwise direction causes small cone 288 to move away from lower finger 276, thereby permitting mounting plate 225 under the bias of coil spring 271 to urge finger 276 away from mirror 203. By this movement of lower finger 276, the third corner of mirror 203 is urged toward rear portion 222 of mirror carriage 215.

When sixth mirror 203 is properly adjusted, a comparator image will be created as described hereinafter. Proper adjustment is effected by looking into the optical system of microscope 300 and then manipulating knobs 292 and 296 as required until the comparator image is properly centered relative to the corneal image. Such adjustment, as well as an explanation of the generation of the corneal image and comparator image, is discussed in detail below.

Figure 6:
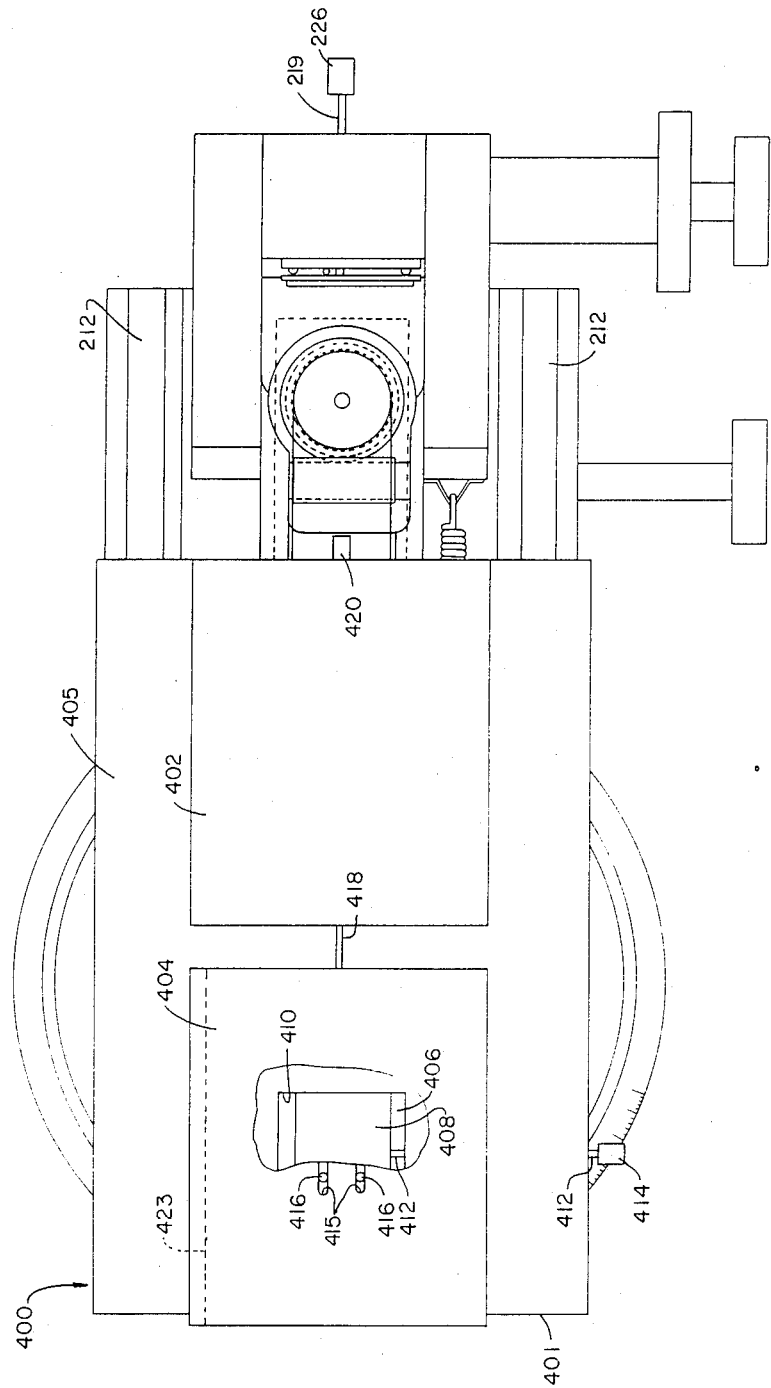
FIG. 6 is a plan view of the top side of the keratometer similar to that of FIG. 1, except that the slidable mounting bracket is shown secured to the device.

Looking next to FIGS. 2 and 6, carriage assembly 400 comprises a base 401 which is is slidably mounted on long rails 212, which are in turn secured to both illuminator assembly 100 and comparator assembly 200, whereby illuminator assembly 100 and comparator assembly 200 are supported by and are slidable beneath base 401 when carriage assembly 400 is secured to microscope 300 as described hereinafter.

A fixed plate 402 is immovably mounted on base 401 and an adjustable plate 404 is movably mounted on base 401 so as to be movable in the X and Y axes along top surface 405 of the base. A rectangular slot 406 (FIG. 6) is formed in base 401. A slide 408 (FIG. 6) is disposed in rectangular slot 406 so as to slidably engage slot walls 410 (only one of which is shown in FIG. 6) of slot 406 whereby the slide is movable along the long dimension of the slot, i.e., along an axis that extends perpendicular to long rails 212. A transversely extending shaft 412 is rotatably mounted in base 401. One end of shaft 412 is secured to a knob 414 and the other end of the shaft is threadedly engaged with slide 408, whereby manipulation of shaft 412 via knob 414 causes slide 408 to slide in slot 406. A pair of elongated slots 415 (FIG. 6) are formed in adjustable plate 404 so as to extend entirely through the plate, and a pair of screws 416 (FIG. 6) are disposed in slots 415 so as to slidably engage the side walls of the slots. Screws 416 are secured to slide 408 so as to extend perpendicular to top surface 405 of base 401. A longitudinally extending shaft 418 is rotatably disposed in an elongate oval aperture (not shown) formed in fixed plate 402. One end of shaft 418 is secured to a knob 420 and the other end of the shaft is threadly engaged with adjustable plate 404.

To move adjustable plate 404 along the X axis, i.e., perpendicular to the elongate dimension of long rails 212, knob 414 is manipulated so as to cause slide 408 to move along the X axis in slot 406. This movement is transmitted via slot 415 and a slot formed in the underside of plate 404 which accepts slide 408 (not shown) and screws 416 to adjustable plate 404 causing the plate to slide on surface 405 along the X axis. The oval aperture in which shaft 418 is disposed is formed so as to permit the shaft to move with adjustable plate 404 along the Y axis.

To move adjustable plate 404 along the Y axis, i.e., parallel to long rails 212, knob 420 is manipulated causing adjustable plate 404 to move toward or away from fixed plate 402. Slots 415 are provided to permit movement of adjustable plate 404 in the Y axis past screws 416 which are secured to slide 408.

The present invention is designed for use with a conventional ophthalmic surgical microscope 300 (FIG. 2), such as that manufactured by Zeiss, typically having a female dovetail mounting bracket 304 (FIG. 2) positioned adjacent to the objective lenses 302 of the microscope. Plate 404 (FIG. 6) of carriage assembly 400 constitutes a male dovetail member configured to be slidably received within the microscope's mounting brackets 304. Inclined side edge 423 (FIG. 6) of plate 404 has a slope corresponding to the slope of an inclined side wall (not shown) of bracket 304 so as to achieve the aforementioned mating between plate 404 and bracket 304. Of course, plate 404 may be modified so as to be securable to the mounting brackets of microscopes other than those manufactured by Zeiss. It is to be appreciated that plate 404 is made adjustable because a microscope's mounting bracket 304 is typically not positioned (relative to objective lenses 302) with the precision necessary to achieve the required alignment between the keratometer and the lenses 302 in order for the invention to function as described below. By properly adjusting plate 404 via the manipulation of knobs 414 and 420, the keratometer may be precisely positioned in a reference plane extending in parallel with the focal plane of objective lenses 302. Proper alignment is achieved when visual inspection reveals that apertures 102 and 103 are coaxially aligned with the objective lenses and when the reflected corneal image (described below) is brightest.

The positioning of the microscope's female dovetail mounting bracket 304 in the Z axis of the aforementioned reference plane (i.e., that axis extending perpendicular to the aforementioned reference plane) is sufficiently precise for the purposes of the present invention. Consequently, Z axis adjustment means are not required or provided on the present keratometer. Therefore, when adjustable plate 404 is secured to bracket 304, and properly adjusted in the X and Y axes relative to objective lenses 302, the keratometer will be properly positioned relative to the microscope's objective lenses 302 so as to permit the creation of a reflected corneal image, as described hereinafter.

Housing 401 (FIG. 6) of carriage assembly 400 is slidably mounted on rails 212 so as to permit the keratometer to be slidable between a first position and a second position. In the first position, shown in FIG. 2, circular housing 101 is positioned directly below objective lenes 302. In the second position, shown in FIG. 6, housing assembly 101 is withdrawn rearward so that it resides below carriage assembly base 401 and housing assembly 101 is withdrawn from the microscope's objective lenses 302 so that no portion thereof is positioned beneath the lenses. Typically, the keratometer is moved to the aforementioned first position during those portions of the ophthalmic surgery or other procedures when it is desirable to have real-time information regarding the curvature of the cornea. For other portions of the surgery or other procedures when the keratometer is not required, the keratometer is moved to the aforementioned second position.

Operation Of The Present Invention

Turning now to FIGS. 2 and 4, to operate the keratometer of the present invention, the device is first secured to the microscope's mounting bracket 304, next it is set in its aforementioned first position wherein the keratometer's circular housing 101 is positioned beneath the microscope's objective lenses 302, and then it is adjusted, via knobs 414 and 420 as described above, so that apertures 102 and 103 are coaxially aligned with the focal axis of binocular objective lenses 302. In this position, first mirror 142 and fifth mirror 201 are positioned in axial alignment with the coaxial illumination light source (not shown) of the microscope 300. Microscope 300 is then positioned above the cornea 502 (FIG. 4) of eye 500 of a patient upon whom corneal examination or surgery is to be performed so that the cornea is axially aligned with midpoint 119 of aperture 115 and so that the microscope's objective lenses 302 may be adjusted to receive a focused image of cornea 502. When microscope 300 is so positioned, illuminator assembly 100 is also positioned so as to generate a reflected corneal image, as described below.

Referring now to FIGS. 2-4 and 7, the reflected corneal image is created by folding a small portion of the light from the microscope's coaxial illumination light source off the mirrors of illuminator assembly 100 so as to intersect cornea 502. Due to the fact that only a small portion of the microscope's coaxial illumination is used by the keratometer, almost the full illumination of the microscope reaches cornea 502 whereby all conventional surgical procedures can be performed with the keratometer disposed in its aforementioned first position beneath objective lenses 302.

Light rays 600 (FIG. 4) from the coaxial illumination source pass through oblong aperture 104 (FIGS. 2 and 3) and into circular cavity 137 (FIG. 4) of cylindrical housing 101 where they intersect first mirror 142. The various light rays identified in FIG. 4 by a single line, such as rays 600, actually comprise a collection of rays, with the identified lines representing the central ray of the collection. Light rays 600 are folded off first mirror 142 forming rays 606 some of which pass through the aperture (not shown) in tab 146 and intersect second mirror 144. By blocking all but those ones of rays 606 that pass through its aperture, tab 146 ensures that only that amount of light necessary for properly forming a reflected corneal image reaches second mirror 144. Rays 606 are folded off second mirror 144 forming rays 608 (FIG. 4) that pass out of circular cavity 137 (FIGS. 2 and 4) to intersect conical third mirror 147.

Rays 608 are folded off conical third mirror 147 so as to extend radially outward therefrom and form an annulus of light 610 (FIG. 4) oriented to reenter circular cavity 137 and intersect annular fourth mirror 139. Posts 113 disposed at the 90, 180 and 270 degree locations (as seen in FIG. 3) block portions of the annulus of light 610, thereby introducing three dark portions (not shown) in the annulus at corresponding angular locations. Consequently, no light reaches the sections of mirror 139 radially aligned with posts 113, these blocked sections of mirror 139 having an arc length of approximately 1-3 degrees. These dark portions in annulus of light 610 are observable in the reflected corneal image, as described below. Annulus of light 610 is then folded off annular fourth mirror 139 forming an annulus of light 612 (FIG. 4) that passes out of circular cavity 137 through curved slots 126 and 134 formed in protractor ring 121 (FIG. 3) to intersect cornea 502. Annulus of light 612 also has three dark portions (not shown) formed in corresponding angular position to the dark portions of the annulus of light 610 created by the blockage of posts 113. Additionally, a fourth dark portion (not shown) exists in annulus of light 612 since no light reflects off the red translucent filter 209 disposed in slot 140 formed in annular mirror 139. This fourth portion is disposed at the 0 degree position (as seen in FIG. 3), whereby dark portions are disposed at 0, 90, 180 and 270 degree positions in the annulus of light 612.

The solid sections 136 (FIG. 3) of annular protractor ring 121 disposed on either side of the two radially extending slots 133 (FIG. 3) prevent portions of the annulus of light 612 from intersecting cornea 502. Where these portions of the annulus of light 612 are blocked, two additional, diametrically opposed, paired, dark portions (not shown) are formed. Each of the paired dark portions comprise two closely spaced dark portions (not shown) spaced from one another by a light portion. This light portion is formed by the portions of annulus of light 612 that pass through slots 133. These paired dark portions in annulus of light 612 are observable in the reflected corneal image, as described below.

The moist convex surface of cornea 502 acts as a reflective surface causing the annulus of light 612 to fold, thereby creating a reflected corneal image 614 (FIG. 4). Corneal image 614 passes upwardly through circular apertures 102 and 103 and into objective lenses 302 of microscope 300, where it is viewable through the optical system of the microscope. Thus, corneal image 614 is created without the use of any optical lenses, other than those already contained in microscope 300. As viewed through microscope 300, seventh mirror 204 does not noticeably block portions of the reflected corneal image 614. This is because seventh mirror 204 is positioned so as to be below the focal plane of objective lenses 302 and therefore produces only an almost imperceptable "shadowing" of image 614.

Figure 7:
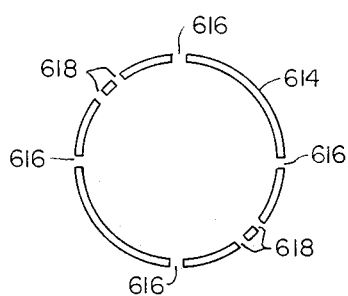
FIG. 7 shows the reflected corneal image of a perfectly spherical cornea, as viewable through the microscope.

When viewed through the optical system of microscope 300, reflected corneal image 614 (FIG. 7) appears as a ring of white light overlaying cornea 502 and having a plurality of illumined segments separated by four dark portions 616. The angular positioning of dark portions 616 correspond to the positioning of the aforementioned dark portions on annuli of light 610 and 612. Corneal image 614 also includes two diametrically opposed, paired dark crossline portions 618 (FIG. 7). These crossline portions 618 correspond in appearance and angular placement to the two paired dark portions (not shown) formed on annulus of light 612 by the solid portions 136 (FIG. 3) of protractor ring 121.

The shape of reflected corneal image 614 is used in determining whether or not an astigmatism exists in, or has been introduced during the surgical procedure to, the eye. When cornea 502 is perfectly spherical, no astigmatism exists and annulus of light 612 is reflected off the cornea so as to form a perfectly spherical corneal image 614, as seen in FIG. 7. If an astigmatism exists in cornea 502 or has been introduced to the cornea during an ophthalmic surgical procedure, annulus of light 612 is reflected off the cornea so as to form an elliptically shaped corneal image 614a, as seen in FIG. 8.

Mirror brackets 143, 145, 202 and 205 may be adjusted by bending as described above so that light rays 600 from the microcope's coaxial illumination source are folded to create the reflected corneal image 614 in the manner described above. Additionally, screws 207 may be loosened and adjustable plates 206 manipulated relative to screws 207 so as to realign seventh mirrors 204 with different radii of apertures102 and 103. Such manipulation of plates 206 may be required to ensure the various aforementioned light rays are folded as described above to create reflected corneal image 614. It is to be appreciated that brackets 143, 145, 202 and 205 and plates 206 are intended to be properly adjusted at the time of manufacture of the device and are not intended to be adjusted by end users of the device.

Figure 8:
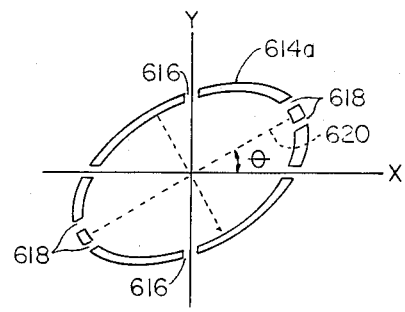
FIG. 8 shows an elliptical reflected corneal image of an astigmatic cornea (it is to be appreciated that the X, Y, major meridian and minor meridian axes of the figure are shown purely for purposes of description and are not viewable through the microscope)
Figure 10:
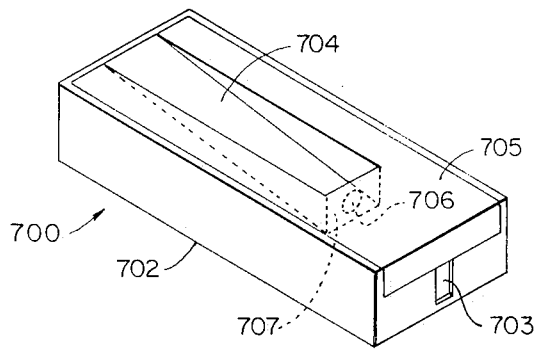
FIG. 10 is an isometric view of a comparator cassette.

Turning next to FIGS. 1, 3, 7 and 8, protractor ring 121 is provided for measuring the angular orientation of the astigmatism of cornea 502. Manipulation of adjustment knob 130 (FIG. 1) causes protractor ring 121 and slots 133 (FIG. 3) formed thereon to rotate about midpoint 119 (FIG. 3) whereby the corresponding dark crossline portions 618 (FIGS. 7 and 8) formed on the reflected corneal image 614 are caused to rotate around image 614. When both pairs of crossline portions 618 intersect the major meridian 620 (FIG. 8) of corneal image 614a, the angular orientation of the astigmatism with respect to the X axis may be calculated by visually comparing which one of the gradation marks 132 (FIG. 1) on protractor ring 121 is most closely aligned with alignment mark 135 (FIG. 2). For example, when the gradation mark 132 at the 30 degree position is aligned with alignment mark 135, the angular orientation of the astigmatism is 30 degrees with respect to the X axis, i.e., the major meridian 620 of corneal image 614a forms an acute angle $\theta$ (FIG. 10) of 30 degrees with the X axis. In FIG. 8, dark portions 618 are shown aligned with the major meridian diameter of corneal image 614a.

Comparator assembly 200 is provided for measuring in diopters the magnitude of the astigmatism. Briefly, this measurement is made by generating and superimposing successive ones of a plurality of spherical light ray annuli of known diameter onto a reflected corneal image 614. As described in detail below, by visually comparing the diameter of the reflected corneal image 614 with the known diameters of the superimposed light ray annuli, the power of the astigmatism may be determined.

Turning now to FIGS. 1-4 and 9, in the generation of the superimposed annular comparison images, light rays 622 (FIG. 4) from the coaxial illumination source of the microscope 300 pass through oblong aperture 104 (FIG. 1) and circular cavity 137 (FIG. 4) to intersect fifth mirror 201. Again, only a relatively small portion of the coaxial illumination intersects mirror 201, thereby ensuring that sufficient light reaches cornea 502 for performing conventional surgical procedures. At fifth mirror 201, rays 622 are folded to create light rays 624. The latter enter circular cavity 137, pass through red translucent filter 209 (FIG. 3) and then pass out of cylindrical housing 101 via slot 140 (FIG. 3) so as to intersect comparator band 238 (FIGS. 1 and 4). When one of the comparator rings 240 (FIG. 4) of comparator band 238 is disposed in radial alignment with slot 252 (FIG. 1) of curved fixed guide 244, light rays 624 pass through the transparent comparator ring and associated numerical optical power equivalents 242, forming annulus of light 625. It is to be appreciated that the annulus of light 625 is red since filter 209 removes all but the red waves of the visible light portion of the electromagnetic wave spectrum.

When sixth mirror 203 is adjusted according to the procedure described below, annulus 625 is folded off mirror 203 to form annulus of light 626. Annulus 626 passes above comparator band 238, through grooves 109 and 110 (FIG. 1), through oblong aperture 104 and into circular apertures 102 and 103, where annulus 626 intersects seventh mirrors 204. Finally, annulus 626 is folded off seventh mirrors 204, creating comparator image light ring 628 (FIGS. 4 and 9) that passes upwardly through circular aperatures 102 and 103 to enter the objective lenses 302 of microscope 300. Thus, comparator image 628 is generated without the use of optical lenses, except for those lenses 302 already contained in microscope 300. As described in greater detail hereinafter, when viewed through microscope 300, comparator image 628 is superimposed on corneal image 614, with both of the images overlaying cornea 502. Annulus 626 and comparator image 628 are both red as they are formed from red annulus 625.

As noted above, in some cases it may be advantageous to block one of the grooves 109 and 110 and/or to remove the one of the seventh mirrors 204 in the one of circular apertures 102 or 103 adjacent the blocked groove. When such a modification of the keratometer is made, comparator image 628 enters only one of the two objective lenses 302 of the microscope, creating only a monoscopic (and not a steroscopic) comparator image. A monoscopic comparator image is often advantageous in that it is easier to focus and compare such an image with the reflected corneal image 614. In some cases, an operating surgeon or other technician using the keratometer may prefer to have a monoscopic comparator image generated if one of their eyes is stronger than the other, or if one of their eyes is damaged so as to be incapable of receiving the comparator image. No observable diminution of the brightness or clarity of comparator image 628 is created by blocking one of grooves 109 or 110 and/or by removing one of the seventh mirrors 204.

In order to generate comparator image 628, several adjustments must first be made on comparator assembly 200, and circular housing 101 must be in its aforementioned first position. Initially, knob 260 (FIGS. 1 and 2) is manipulated so that one of comparator rings 240 is positioned in radial alignment with slot 252 of curved fixed guide 244. Next, knobs 226 (FIGS. 1 and 2), 292 (FIGS. 1 and 2) and 296 (FIGS. 1 and 2) must be manipulated so that the angle of incidence of annulus 625 at sixth mirror 203 is such that annulus 626 is folded off mirror 203 so as to intersect seventh mirrors 204.

Manipulation of knob 226 changes the size of annulus 626 and comparator image 628 as measured at any selected point along the paths of travel of these annuli of light. By selectively manipulating knob 226, the comparator image 628 intersecting the focal plane of the objective lenses of a conventional surgical microscope may be sized so as to appear as a focused annular image when viewed through the microscope. Mirror carriage 215, threaded shaft 219 and knob 226 are configured so that annular comparator image 628 may not be brought into focus in those surgical microscopes having objective lens with focal lengths of other than between 175 mm to 200 mm, thereby avoiding the possibility of obtaining an incorrect reading of the optical condition of cornea 502.

Proper adjustment of sixth mirror 203 can be best effected by visually noting in the microscope's optical system the change in brightness of comparator image 628 that occurs as a result of the manipulation of knobs 226, 292 and 296. Sixth mirror 203 is properly adjusted when comparator image 628 is at the brightest level.

Once comparator image 628 is coaxially superimposed on corneal image 614, measurement may be made as to the power of the astigmatism.

Figure 9:
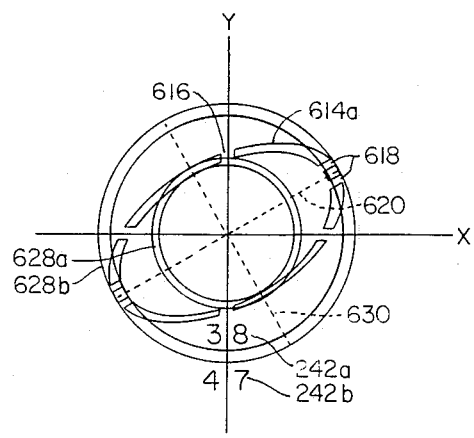
FIG. 9 shows the elliptical corneal image of FIG. 8 with two comparator images superimposed thereon (it is to be appreciated that the X, Y, major meridian, minor meridian axes and the two comparator images are shown purely for purposes of description—in practice, only one comparator image is superimposed on the corneal image, and the above-identified axes are not viewable)

To calculate the power of the astigmatism, knob 260 is manipulated, driving comparator band 238 as described above, whereby successive ones of comparator rings 240 (FIG. 4) are aligned with slot 252 (FIG. 1) of curved fixed guide 244. By this presentation of rings 240, successive ones of comparator image 628 having successively increasing or decreasing diameter (depending on the direction in which knob 260 is manipulated) are superimposed on the reflected corneal image 614. The diameters of successive ones of comparator image 628 are compared with the minor meridian diameter 630 (FIG. 9) of the corneal image 614a (FIG. 9). When the comparator image 628 is found whose diameter most closely approximates the minor meridian diameter of corneal image 614a, as shown in FIG. 9, the diopter numeral 242 (FIG. 9) disposed immediately below that image 628 is recorded. In FIG. 9, this comparison image is identified as 628a and the diopter numeral is identified as 242a. Next, knob 260 is manipulated and a similar comparison is made with respect to the major meridian diameter 620 (FIG. 9) of corneal image 614a. When the one of comparator image 628 is found whose diameter most closely approximates the major meridian diameter of corneal image 614a, the diopter numeral 242 associated with that image is again recorded. In FIG. 9, this comparator image 628 is identified as 628b and the diopter numeral is identified as 242b. The power, in diopters, of the astigmatism of cornea 502 is then calculated by subtracting the diopter number of the comparator image 628a associated with the minor meridian diameter of the corneal image 614a from the diopter number of the comparator image 628b associated with the major meridan diameter of corneal image 614a. It is to be appreciated that the two comparator images 628a and 628b are shown superimposed on corneal image 614a for purposes of description only; in practice, only one comparison image 628 will be superimposed on the corneal image 614a at a given time when viewed through microscope 300.

It is to be appreciated that, in addition to supporting circular plate 112, posts 113 create the dark portions 616 formed on corneal image 614, as described above. Comparison measurement is facilitated by comparing the interface of the edges of dark portions 616 with the reflected corneal image 614. Also, by superimposing a red comparator image 628 on a white reflected corneal image 614, comparison measurement is more readily effected.

It is to be appreciated that certain changes may be made to the aforementioned keratometer without departing from the scope of the invention.

Thus, for example, comparator assembly 200 may be modified to permit quick replacement of one comparator band 238 with another comparator band. To this end, comparator band 238, curved fixed guide 244 and rotatable hub 246 are removed and a comparator cassette 700 (FIGS. 10 and 11) is substituted therefor.

Cassette 700 comprises a housing 702 having a slot 703 formed in one end thereof and having an inclined raised portion 704 formed on the top surface 705 of housing 702. An aperture 706 is formed in the end surface 707 of raised portion 704. An optical lense (not shown) may be disposed within aperture 706 should magnification of the comparator image be desired. Disposed within comparator cassette 700 are a curved fixed guide 744 (FIG. 11) having a slot 752 (FIG. 11) formed therein and a rotatable hub 746 (FIG. 8) having a keyway 768 (FIG. 8) formed therein for engagement with a corresponding sized key (not shown) secured to circular gear 254. Fixed guide 744 is disposed within housing 702 so that slot 752 is aligned with the slot 703 formed in housing 702. A comparator band 738 is rotatably supported on curved fixed guide 744 and is supported by and drivingly engages rotatable hub 746. Radially extending teeth 761 are provided on the peripheral edge of rotatable hub 746 for engaging correspondingly positioned slots (not shown) on comparator band 738, thereby facilitating the transmission of rotational drive from the hub to the comparator band.

Cassette housing 702 is sized so as to fit snugly in cavity 211 (FIG. 1) of comparator assembly 200. During the insertion of cassette 700 into cavity 211, keyway 768 is engaged with a key (not shown) secured to circular gear 254 (FIG. 1), whereby rotational drive may be transmitted from gear 254 to hub 746. Comparator band 738 is indexably adjustable via knob 260 in the same manner as comparator band 238, as described above.

Figure 11:
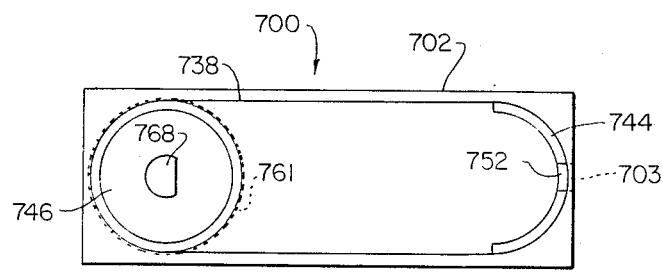
FIG. 11 is a plan view of the comparator cassette, with the top surface of the cassette removed for purposes of illustration.

Referring to FIGS. 1-4, 9, 10 and 11, when comparator cassette 700 is used in place of the aforementioned comparator band 238, curved fixed guide 244 and rotatable hub 246, rays 622 intersect fifth mirror 201 where they are folded to create the light rays 624. The latter enter circular cavity 137, pass through red translucent filter 209 (FIG. 3) disposed in slot 140 (FIG. 3) formed in cylindrical housing 101, pass through slot 703 (FIGS. 10 and 11) formed in comparator cassette housing 702, and then intersect comparator band 738 (FIG. 11). When one of the comparator rings (not shown) of comparator band 738 is disposed in radial alignment with slot 752 (FIG. 8) of curved fixed guide 744, light rays 624 pass through the comparator ring creating annulus of light 625 that intersects sixth mirror 203. As noted above, filter 209 makes the rays 624 passing through comparator band 738 red in color.

Comparator cassette 700 permits the present invention to be readily modified for use in different types of ophthalmic surgeries. For instance, it may be desirable to use a first comparator cassette for cataract surgery and a second cassette for radial keratomoty. In the first comparator cassette, the comparator rings and numerical optical power equivalents formed on comparator band 738 would be of the type used on comparator band 238, as described above. The second comparator cassette is specifically designed for use in radial keratomoty by providing radially extending slits (not shown) disposed within the circumference of the comparator rings whereby the comparator image viewable through microscope 300 includes radially extending visual incision guide lines. Since these guides are superimposed on the reflected corneal image, as described above, they provide a pattern the surgeon can follow in performing the radial incising of the cornea. Other ophthalmic surgeries or other procedures may require the use of other comparator image patterns for which additional comparator cassettes 700 may be provided.

Figure 12:
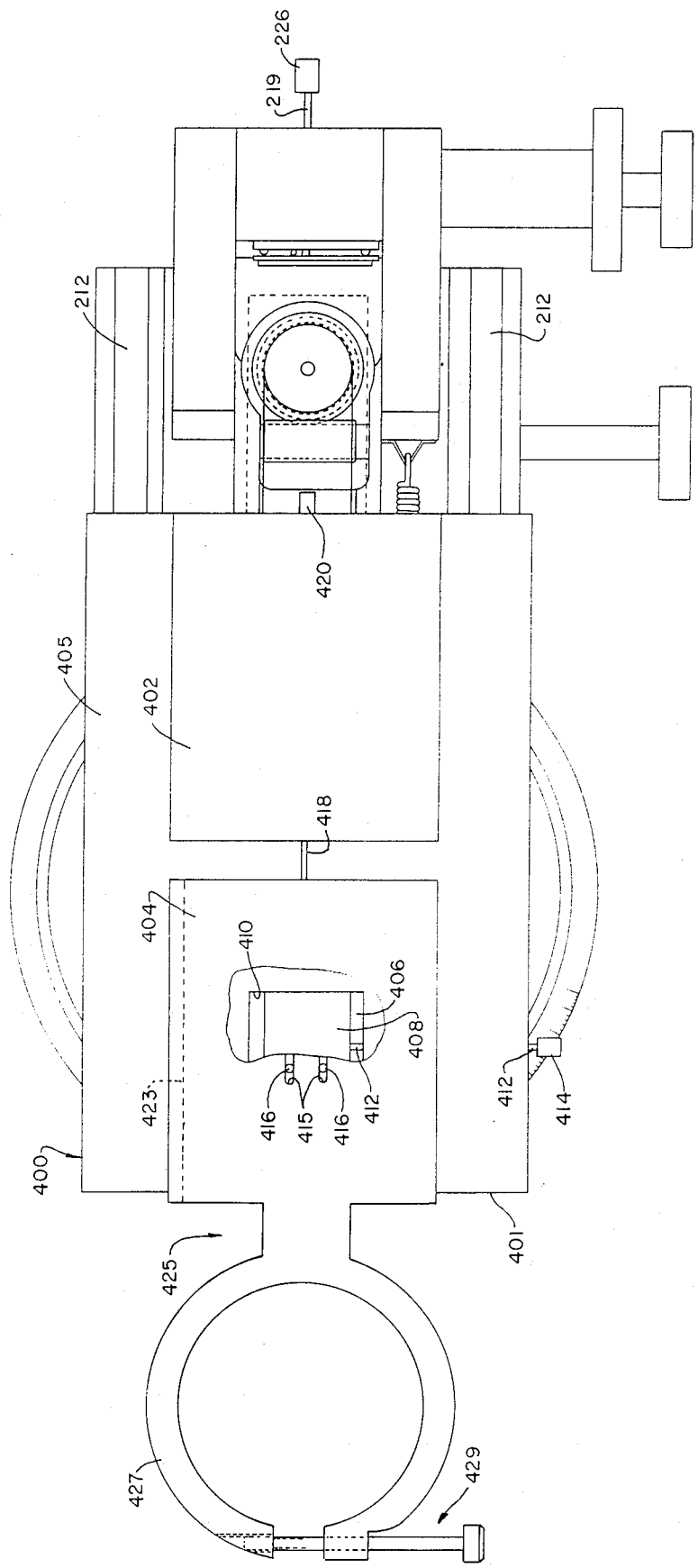
FIG. 12 is a plan view of the top side of the keratometer and is identical to that of FIG. 6, except that sliding plate 404 (hereinafter described in detail) has been replaced with an alternative form of sliding plate which includes an extension 425 having a collar element 427 (all hereinafter described in detail)

It is also anticipated that one might change the manner in which the keratometer is attached to the microscope. In the embodiment described above, slidable carriage assembly 400 is secured to microscope 300 by sliding plate 404 (which acts as a male dovetail member) into the microscope's mounting bracket 304 (which acts as a female mounting bracket). Alternatively, and looking now at FIG. 12, plate 404 could be provided with an extension 425 which is preferably formed integral with plate 404 and which terminates in a collar element 427 whose sizing is determined by the disposition of an associated screw 429. A keratometer provided with such an extension 425 can be mounted to the microscope by fitting collar 427 over the objective lenses 302 of the microscope and locking the collar in place by manipulation of screw 429. Such an arrangement permits the keratometer to be mounted to a microscope in a manner which always properly references it to the optical axis of the microscope.

Figure 13:
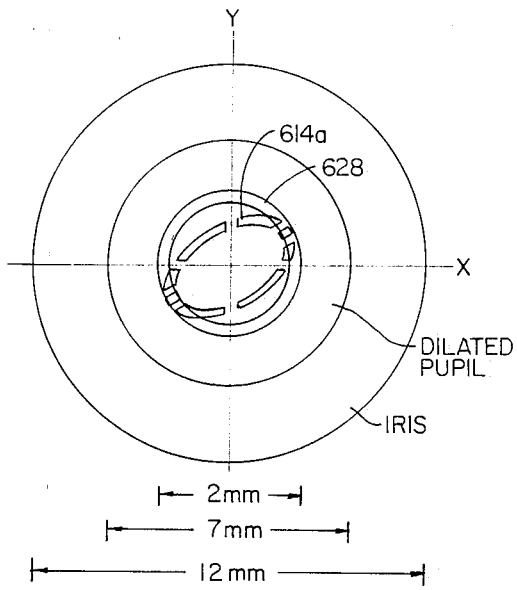
FIG. 13 is a view identical to that of FIG. 9, except that it includes only one comparator image (i.e., comparator image 628b) and shows the reflected corneal image and the comparator image superimposed on the cornea itself.
Figure 14:
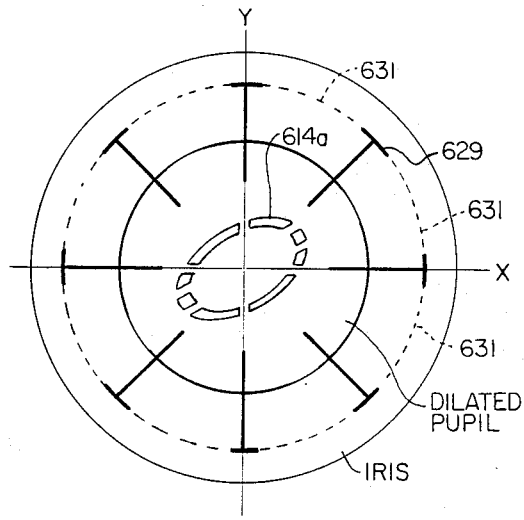
FIG. 14 is a view identical to that of FIG. 13, except that it shows an alternative form of comparator image which is magnified in size relative to the reflected corneal image and the cornea, as might be the case if the comparator cassette included an appropriate optical element (hereinafter described in detail)
Figure 15:
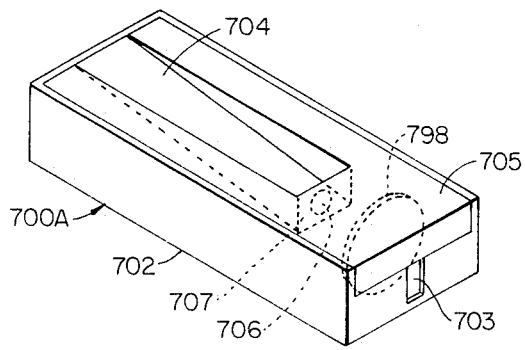
FIG. 15 is a view like that of FIG. 10, except that the comparator cassette includes an optical element 798 (hereinafter described in detail)
Figure 16:
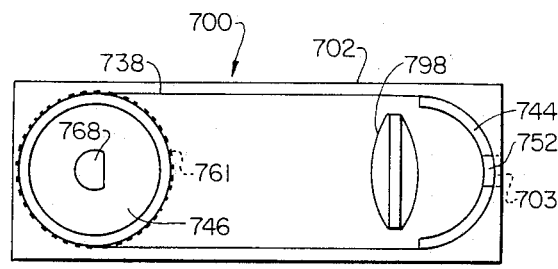
FIG. 16 is a view like that of FIG. 11, except that the comparator cassette includes the same optical element 798 shown in FIG. 15.

It is also anticipated that one might include an appropriate optical element within a comparator cassette so that the ring of light comprising the comparator image is of increased (or decreased) size relative to the image of cornea 502 which is simultaneously presented to the microscope. More particularly, the comparator cassette 700 described above provides a comparator image 628 in the form of a ring of light which, when superimposed on the image of cornea 502, appears to be approximately 3 mm in diameter (see FIG. 13). For some purposes, e.g. radial keratomoty, it may be desirable to increase the size of the comparator image relative to the size of the image of cornea 502, e.g. so that the comparator image has a diameter of 10 mm (see FIG. 14, where the comparator image comprises a radial pattern 629 which may or may not include the arc portions 631). This effect can be achieved by including an appropriate optical element within the comparator cassette, whereby the optical element will serve to increase (or decrease) the size of the comparator image relative to the size of the cornea 502. Looking next at FIGS. 15 and 16, there is shown a comparator cassette 700a which is substantially identical to the aforementioned comparator cassette 700, except that comparator cassette 700a includes an optical element 798 which is disposed in a groove (not shown) formed in the floor of the cassette. Optical element 798 is disposed so that it intercepts light passing through aperture 703, and appropriately magnifies (or diminishes) it so as to create the desired alteration of light rays 624.

Figure 17:
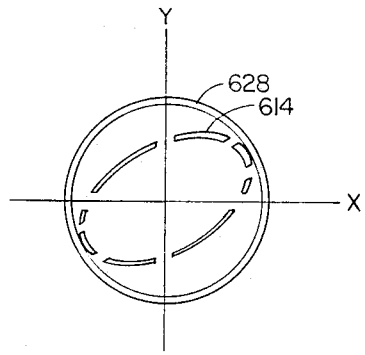
FIG. 17 is a view like that of FIG. 9, except that only one comparator image (i.e., comparator image 628b) is shown, and that comparator image appears as a ring of white light, as might be the case if red filter 209 were replaced with a diffusion filter (hereinafter described in detail).

It is also anticipated that one might replace translucent red filter 209 with a diffusion filter, so that comparator image 628 appears as a white ring of light rather than a ring of red light. The diffused comparator image could be compared with the white reflected corneal image 614 by positioning the inner diameter edge of comparator image 628 against the outer diameter edge of reflected corneal image 614, as shown in FIG. 17.

Finally, it is to be appreciated that the comparator band 238 could be modified from that disclosed above so that the diopter number is positioned above, or to one side of, comparator image 628, rather than below comparator image 628, as previously shown.

Still other changes will be obvious to persons skilled in the art and are considered to be within the scope of the present invention.

What is claimed is:

1. A keratometer for measuring the curvature of the cornea of the eye whereby an astigmatic condition may be detected and the power and angular orientation of the astigmatism may be measured, the keratometer being adapted for use with an ophthalmic surgical microscope disposed adjacent the eye and having a mounting bracket, a source of coaxial illumination and an optical system having a focal plane and objective lenses, said keratometer comprising;

illuminator means for generating a first annulus of light rays defining an annular corneal image and for causing said first annulus to pass into the focal plane of said microscope so as to permit viewing of said corneal image in the optical system of said microscope, said first annulus having radii of curvature corresponding to the radii of curvature of the cornea of said eye;

comparator means for generating a plurality of second annuli of light rays defining a corresponding respective plurality of annular comparator images, each of which images is separated from the immediately preceding and the immediately following comparator image by the absence of a comparator image, and for causing each of said plurality of comparator images to pass successively into the focal plane of said microscope so that each of said plurality of comparator images may be coaxially aligned with said firs annulus whereby said corneal image may be viewed in the optical system of the microscope and compared with successive ones of said plurality of comparator images to determine the power of the astigmatism; and frame means for securing said illuminator means and said comparator means together in fixed spatial relation to one another and for securing said illuminator means and said comparator means to said microscope so as to permit generation of said corneal image and said comparator image.

2. A keratometer according to claim 1 further comprising means for blocking at least two diametrically-opposed portions of said first annulus of light so as to provide at least two diametrically-opposed dark portions on said annular corneal image which may be used for measuring the angular orientation of the astigmatism.

3. A keratometer according to claim 1 wherein said illuminator means and said comparator means are slidably mounted to said frame means so as to permit said illuminator means and comparator means to be moved between a first position wherein said illuminator means is positioned beneath and is aligned with the central axis of the objective lenses of said microscope and a second position wherein said illuminator means is positioned off to one side of and is not aligned with the central axis of the objective lenses of the microscope.

4. A keratometer according to claim 1 wherein said frame means further comprises connection means for adjustably securing said frame means to said mounting bracket so as to permit said keratometer to be reciprocatably moved along a reference plane extending in parallel with the focal plane of the optical system of the microscope between a first position where said illuminator means is aligned with said objective lenses so that said corneal image and comparator image are viewable in the optical system of said microscope and a second position where said illuminator means is not aligned with said objective lens and where said comparator image is not viewable in the optical system of said microscope, said connection means being configured to matingly engage said mounting bracket.

5. A keratometer according to claim 1 wherein said comparator means comprises:

a housing;

an opaque comparator band having a plurality of transparent portions defining a plurality of transparent rings; and comparator band support means mounted to said housing for supporting said comparator band so that said transparent ring is disposed in a predetermined location.

6. A keratometer according to claim 5 wherein:

said opaque comparator band comprises an endless band having a plurality of differently sized transparent portions formed thereon defining a corresponding respective plurality of differently sized transparent rings;

said comparator band support means comprises guide means for slidably supporting said endless band and hub means for supporting and driving said endless band so as to move successive ones of said plurality of transparent rings to said predetermined location; and said comparator means further includes drive means coupled to said hub means for rotatably driving said hub means.

7. A keratometer according to claim 5 wherein said endless band further comprises a plurality of transparent numerical optical power equivalents formed adjacent each of said plurality of transparent rings, each of said plurality of numerical optical power equivalents including numerals identifying the size of the corresponding respective transparent ring with which it is associated.

8. A keratometer according to claim 5 wherein:

said illuminator means comprises a first plurality of mirrors configured and aligned with one another to fold a first small portion of said coaxial illumination so as to generate said first annulus of light rays; and said comparator means comprises a second plurality of mirrors for folding a second small portion of said coaxial illumination so that said second small portion passes through one of said plurality of transparent rings positioned in said predetermined location thereby generating said second annulus of light rays.

9. A keratometer according to claim 8 wherein said illuminator means comprises means for measuring the angle of orientation of the astigmatism of the cornea.

10. A keratometer according to claim 9 wherein said illuminator means comprises means for blocking portions of said first small portion of coaxial illumination so as to create a plurality of dark portions in said first annulus, said portions being spaced apart a predetermined distance from one another.

11. A keratometer for measuring the curvature of the cornea of the eye whereby an astigmatic condition may be detected and the power and angular orientation of the astigmatism may be measured, the keratometer being adapted for use with an ophthalmic surgical microscope disposed adjacent the eye and having a mounting bracket, a source of coaxial illumination and an optical system having a focal plane and objective lenses, said keratometer comprising:

a mirror housing having an aperture extending entirely therethrough;

first mirror means for reflecting a first portion of the light rays of the coaxial illumination of the microscope so as to cause said first portion to travel along a first path, said first mirror means being secured to said housing and disposed in said aperture;

second mirror means for reflecting said first portion traveling along said first path so as to cause said first portion to travel along a second path, said second mirror means being secured to said housing so that said first portion traveling along said first path intersects said second mirror;

convex conical third mirror means for reflecting said first portion traveling along said second path so as to create a first annulus of light that travels along a third path, said convex mirror means being secured to said housing so that said first portion traveling along said second path intersects said convex conical third mirror means;

annular fourth mirror means for reflecting said first annulus of light traveling along said third path so as to cause said first annulus of light to travel along a fourth path that intersects said cornea whose moist reflective surface reflects said first annulus of light causing said first annulus to travel along an upward path, said annular fourth mirror means being secured to said housing so that said first annulus of light traveling along said third path intersects said annular fourth mirror means;

a comparator housing secured to said mirror housing in fixed spatial relation thereto;

comparator band means comprising an opaque surface having a plurality of transparent portions defining a plurality of transparent rings, said comparator band means being secured to said housing so that said transparent ring is disposed in a predetermined position;

fifth mirror means for reflecting a second portion of the light rays of the coaxial illumination of the microscope so as to cause said second portion to travel along a fifth path that passes through said transparent ring disposed in said predetermined position whereby a second annulus of light is created that travels along said fifth path, said fifth mirror means being secured to said mirror housing and disposed in said aperture;

sixth mirror means for reflecting said second annulus of light so as to cause said second annulus of light to travel along a sixth path, said sixth mirror means being secured to said comparator housing so that said second annulus of light traveling along said fifth path intersects said sixth mirror means;

seventh mirror means for reflecting said second annulus of light traveling along said sixth path so as to cause said second annulus of light to travel along an upward path along which said first annulus of light travels in coaxially superimposed relation with said first annulus of light; and frame means adapted for supporting said mirror housing and said comparator housing so that (1) said first mirror means is positioned for reflecting said first portion of the light rays of the coaxial illumination, (2) said fifth mirror is positioned for reflecting said second portion of the light rays of the coaxial illumination, and (3) said first annulus of light traveling along said upward path and said second annulus of light traveling along said upward path enter the objective lenses of the microscope.

12. A keratometer according to claim 11 wherein said comparator band means comprises an endless band having a plurality of transparent portions formed thereon defining a corresponding plurality of transparent rings, and further including comparator band drive means for causing said endless band to index so as to selectively position one of said plurality of transparent rings in said predetermined position.

13. A keratometer according to claim 12 wherein said plurality of transparent rings comprises differently sized transparent rings, and further wherein transparent numerical optical equivalents are formed adjacent each transparent ring indicating in diopters the size of the associated ring.

14. A keratometer according to claim 13 further comprising protractor ring means for measuring the angle of orientation of an astigmatism of the cornea.

15. A keratometer according to claim 14 wherein said protractor ring means comprises;
  means for blocking two diametrically opposed portions of said first annulus traveling along said fourth path so as to create two diametrically opposed dark portions on said first annulus traveling along said upward path;
  an annular portion rotatably mounted to said mirror housing having a plurality of angular gradation marks and associated angular degree numerals disposed adjacent a peripheral edge of said annular portion, said means for blocking opposed portions being mounted on said annular portion; and
  protractor ring adjustment means mounted on said mirror housing and coupled to said protractor ring means for causing said annular portion to rotate.

16. A keratometer according to claim 15 further comprising adjustment means coupled to said sixth mirror means for adjusting said sixth mirror means so that said second annulus of light traveling along said sixth path is oriented to intersect said seventh mirror means.

17. A keratometer according to claim 16 wherein said frame means comprises carriage means slidably mounted to said comparator housing, said adjustment means and said sixth mirror means being mounted to said carriage means so as to be movable therewith, said carriage means further including selectively adjustable focus means for slidably moving said carriage within a range so as to position said sixth mirror means so that said second annulus of light traveling along said upward path is sized at said focal plane of said objective lenses so as to appear as a focused image when viewed through said microscope.

18. A keratometer according to claim 17 wherein said range of movement of said carriage is selected to ensure that said second annulus of light will appear as a focused image only in microscopes having an objective lens focal length ranging from 175 mm to 200 mm.

19. A keratometer according to claim 12 wherein said comparator band drive means comprises:
  a hub rotatably mounted to said comparator housing so as to drivingly engage said endless band;
  guide means adjustably mounted to said comparator housing for slidably supporting said endless band;
  gear means rotatably mounted to said comparator housing so as to drivingly engage said hub; and
  handle means rotatably disposed in said comparator housing and secured to said gear means so that rotation of said handle causes said gear means to rotate.

20. A keratometer according to claim 19 wherein said hub is adapted to releasably engage said gear means, said keratometer further comprising a comparator cassette adapted to be releasably secured to said comparator housing, said hub being rotatably mounted to said comparator cassette, said guide means being adjustably mounted to said comparator cassette, and said endless band being supported on said hub and said guide means so that successive ones of said plurality of transparent rings may be moved to said predetermined location when said comparator cassette is secured to said comparator housing.

21. A keratometer according to claim 11 wherein said frame means comprises:
   rail means secured to said mirror housing and said comparator housing;
   a frame housing slidably mounted to said rail means;
   a coupling member movably mounted to said frame means so as to be movable along a plane extending in parallel with the focal plane of the optical system of the microscope, said coupling member being adapted for attachment to said mounting bracket; and
   alignment drive means connected to said coupling member for causing said coupling member to move along said plane so as to permit said frame housing to be moved so that (1) said first mirror means and said third mirror means may be aligned with said source of coaxial illumination and (2) said fourth mirror means may be aligned with the optical axis of said objective lenses.

22. A keratometer according to claim 21 wherein said rail means is sized to permit said keratometer to be moved between a first position wherein said fourth mirror means are aligned with the optical axis of said objective lenses when said keratometer is attached to said microscope and a second position wherein no portion of said keratometer is positioned beneath said objective lenses when said keratometer is secured to said microscope.

23. A keratometer for measuring the curvature of the cornea of the eye whereby an astigmatic condition may be detected and the power and angular orientation of the astigmatism may be measured, the keratometer being adapted for use with an ophthalmic surgical microscope disposed adjacent the eye and having a mounting bracket, a source of coaxial illumination and an optical system having a focal plane and objective lenses, said keratometer comprising:
   illuminator means for generating a first annulus of light rays defining an annular corneal image and for causing said first annulus to pass into the focal plane of said microscope so as to permit viewing of said corneal image in the optical system of said microscope, said first annulus having radii of curvature corresponding to the radii of curvature of the cornea of said eye;
   comparator means for generating a plurality of second annuli of light rays defining a corresponding respective plurality of annular comparator images and for causing each of said plurality of second annuli to pass into the focal plane of said microscope so as to be superimposed on said first annulus whereby said corneal image may be viewed in the optical system of the microscope and compared with successive ones of said plurality of comparator images to determine the power of the astigmatism; and
   frame means for securing said illuminator means and said comparator means together in fixed spatial relation to one another and for securing said illuminator means and said comparator means to said microscope so as to permit generation of said corneal image and said comparator image,
   wherein said illuminator means and said comparator means use only the coaxial illumination of said microscope in generating said annular corneal image and said annular comparator image, respectively.

24. A keratometer according to claim 23 wherein said comparator means comprises:
   a housing;
   an opaque comparator band having a plurality of transparent portions defining a plurality of transparent rings; and
   comparator band support means mounted to said housing for supporting said comparator band so that said transparent ring is disposed in a predetermined location.

25. A keratometer according to claim 24 wherein:
   said opaque comparator band comprises an endless band having a plurality of differently sized transparent portions formed thereon defining a corresponding respective plurality of differently sized transparent rings;
   said comparator band support means comprises guide means for slidably supporting said endless band and hub means for supporting and driving said endless band so as to move successive ones of said plurality of transparent rings to said predetermined location; and
   said comparator means further includes drive means coupled to said hub means for rotatably driving said hub means.

26. A keratometer according to claim 24 wherein said endless band further comprises a plurality of transparent numerical optical power equivalents formed adjacent each of said plurality of transparent rings, each of said plurality of numerical optical power equivalents including numerals identifying the size of the corresponding respective transparent ring with which it is associated.

27. A keratometer according to claim 24 wherein:
   said illuminator means comprises a first plurality of mirrors configured and aligned with one another to fold a first small portion of said coaxial illumination so as to generate said first annulus of light rays; and
   said comparator means comprises a second plurality of mirrors for folding a second small portion of said coaxial illumination so that said second small portion passes through one of said plurality of transparent rings positioned in said predetermined location thereby generating said second annulus of light rays.

28. A keratometer according to claim 27 wherein said illuminator means comprises means for measuring the angle of orientation of the astigmatism of the cornea.

29. A keratometer according to claim 28 wherein said illuminator means comprises means for blocking portions of said first small portion of coaxial illumination so as to create a plurality of dark portions in said first annulus, said portions being spaced apart a predetermined distance from one another.

30. A keratometer for measuring the curvature of the cornea of the eye whereby an astigmatic condition may be detected and the power and angular orientation of the astigmatism may be measured, the keratometer being adapted for use with an ophthalmic surgical microscope disposed adjacent the eye and having a mounting bracket, a source of coaxial illumination and an optical system having a focal plane and objective lenses, said keratometer comprising:
   illuminator means for generating a first annulus of light rays and for causing said first annulus to intersect said cornea whose moist reflective surface reflects said first annulus into the focal plane of said microscope as a second annulus of light rays having radii of curvature corresponding to the radii of curvature of said eye;

comparator means for generating a plurality of predetermined light ray patterns and for successively introducing ones of said plurality of predetermined light ray patterns into said focal plane of said microscope in conjunction with said second annulus of light rays so as to permit said second annulus of light rays to be compared to said ones of said plurality of predetermined light ray patterns;

frame means for securing said illuminator means and said comparator means together in fixed spatial relation to one another and for securing said illuminator means and said comparator means to said microscope so as to permit introduction of said second annulus of light rays and said plurality of predetermined light ray patterns into said focal plane of said microscope; and wherein said illuminator means and said comparator means use only the coaxial illumination of said microscope in generating said first annulus of light rays and said plurality of predetermined light ray patterns, respectively.

31. A keratometer for measuring the curvature of the cornea of the eye whereby an astigmatic condition may be detected and the power and angular orientation of the astigmatism may be measured, the keratometer being adapted for use with an opthalmic surgical microscope disposed adjacent the eye and having a mounting bracket, a source of coaxial illumination and an optical system having a focal plane and objective lenses, said keratometer comprising:

illuminator means for generating a first annulus of light rays and causing said first annulus to intersect said cornea whose moist reflective surface reflects said first annulus into the focal plane of said microscope as a second annulus of light rays having radii of curvature corresponding to the radii of curvature of said eye;

comparator means for generating a plurality of third annuli of light rays and for causing each of said plurality of third annuli of light rays to pass into the focal plane of said microscope in conjunction with said second annulus of light rays so as to permit said second annulus of light rays to be compared to successive ones of said plurality of third annuli of light rays;

and frame means for securing said illuminator means and said comparator means together in fixed spatial relation to one another and for securing said illuminator means and said comparator means to said microscope so as to permit introduction of said second annulus of light rays and each of said plurality of third annuli of light rays into said focal plane of said microscope; and wherein said illuminator means and said comparator means use only the coaxial illumination of said microscope in generating said first annulus of light rays and said predetermined pattern of light rays, respectively.

32. A keratometer for measuring the curvature of the cornea of the eye whereby an astigmatic condition may be detected and the power and angular orientation of the astigmatism may be measured, the keratometer being adapted for use with an ophthalmic surgical microscope disposed adjacent the eye and having a mounting bracket, a source of coaxial illumination and an optical system having a focal plane and objective lenses, said keratometer comprising:

illuminator means for generating a first annulus of light rays defining an annulus corneal image and for causing said first annulus to pass into the focal plane of said microscope so as to permit viewing of said corneal image in the optical system of said microscope, said first annulus having radii of curvature corresponding to the radii of curvature of the cornea of said eye;

comparator means, having a member comprising a plurality of transparent annular images, or generating a plurality of second annuli of light rays defining a corresponding respective plurality of annular comparator images using said member, and for causing each of said plurality of comparator images to pass successively into the focal plane of said microscope so as to be positioned proximate to said first annulus whereby said corneal image may be viewed in the optical system of the microscope and compared with successive ones of said plurality of comparator images to determine the power of the astigmatism; and frame means for securing said illuminator means and said comparator means together in fixed spatial relation to one another and for securing said illuminator means and said comparator means to said microscope so as to permit generation of said corneal image and said comparator image.

* * * * *